United States Patent
Eckhouse et al.

(10) Patent No.: US 6,514,243 B1
(45) Date of Patent: *Feb. 4, 2003

(54) METHOD AND APPARATUS FOR ELECTROMAGNETIC TREATMENT OF THE SKIN, INCLUDING HAIR DEPILATION

(75) Inventors: Shimon Eckhouse, Haifa (IL); Hillel Bachrach, Needham, MA (US)

(73) Assignee: Lumenis Ltd., Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 09/505,998

(22) Filed: Feb. 17, 2000

Related U.S. Application Data

(63) Continuation of application No. 08/912,764, filed on Aug. 18, 1997, now Pat. No. 6,280,438, which is a continuation-in-part of application No. 08/508,129, filed on Jul. 27, 1995, now Pat. No. 5,720,772, which is a continuation-in-part of application No. 08/477,479, filed on Jun. 7, 1995, now Pat. No. 5,620,478, which is a continuation of application No. 08/473,532, filed on Jun. 7, 1995, now Pat. No. 5,755,751, which is a continuation of application No. 08/383,509, filed on Feb. 3, 1995, now Pat. No. 5,626,631, which is a continuation-in-part of application No. 07/964,210, filed on Oct. 20, 1992, now Pat. No. 5,405,368, which is a continuation-in-part of application No. 08/412,519, filed on Mar. 29, 1995, now Pat. No. 5,683,380.

(51) Int. Cl.[7] ............................................... A61B 18/18
(52) U.S. Cl. ................................ 606/9; 606/3; 606/10; 607/88
(58) Field of Search .............................. 606/2, 3, 9, 10, 606/11, 12, 13, 17, 18, 19; 607/88, 90

(56) References Cited

U.S. PATENT DOCUMENTS

| | | |
|---|---|---|
| 1,651,385 A | 12/1927 | Goodrich |
| 3,327,712 A | 6/1967 | Kaufman |
| 3,538,919 A | 11/1970 | Meyer |
| 3,693,623 A | 9/1972 | Harte et al. |
| 3,818,914 A | 6/1974 | Bender |
| 3,821,510 A | 6/1974 | Muncheryan |

(List continued on next page.)

FOREIGN PATENT DOCUMENTS

| | | |
|---|---|---|
| DE | 2717421 | 11/1978 |
| DE | 3906860 | 9/1989 |
| EP | 0052765 | 10/1981 |
| EP | 0324490 | 1/1989 |
| EP | 0724894 | 1/1989 |
| EP | 0565331 | 10/1993 |
| EP | 0736308 | 10/1996 |
| FR | 2571264 | 4/1986 |
| JP | 55117166 | 9/1980 |
| SE | 416861 | 1/1967 |
| SE | 3804732 | 8/1989 |
| SE | 465953 | 11/1991 |
| WO | WO 8900871 | 2/1989 |
| WO | WO 9115264 | 10/1991 |

OTHER PUBLICATIONS

Gustafsson et al. "A Variable Pulsewidth Vascular System For Dermatology", SPIE vol. 2128, pp. 186–196 (1994).
Lahaye et al. "Optimal Laser Parameters for Port Wine Stain Therapy: a Theoretical Approach", Phys. Med. Biol., 1985, vol. 30, pp. 573 to 587. (1985).
Van–Gemert et al. "Treatment of Port–Wine Stains: Analysis", Medical Instrumentation, vol. 21, pp. 213–217. (1987).
Diffusion of Light in Turbid Material, A. Ishimaru, Applied Optics 1989, vol. 28, No. 12, pp. 2210–2215.

*Primary Examiner*—Eric F. Winakur
(74) *Attorney, Agent, or Firm*—Eitan, Pearl, Latzer & Cohen-Zedek

(57) ABSTRACT

Apparatus and methods for electromagnetic skin treatment, including the removal of hair. Devices include pulsed light sources such as flashlamps for providing electromagnetic treatment of the skin, including hair removal. The devices and methods provide for the removal of large numbers of hairs at the same time, rather than on a hair by hair basis.

2 Claims, 13 Drawing Sheets

U.S. PATENT DOCUMENTS

| | | | |
|---|---|---|---|
| 3,834,391 A | | 9/1974 | Block |
| 3,916,143 A | | 10/1975 | Farrel |
| 4,022,534 A | | 5/1977 | Kishner |
| 4,233,493 A | | 11/1980 | Nath |
| 4,241,382 A | | 12/1980 | Daniel |
| 4,298,005 A | | 11/1981 | Mutzhas |
| 4,388,924 A | | 6/1983 | Weissman et al. |
| 4,608,978 A | * | 9/1986 | Rohr .............................. 606/9 |
| 4,617,926 A | | 10/1986 | Sutton |
| 4,669,466 A | | 6/1987 | L'Esperance |
| 4,686,986 A | | 8/1987 | Fenyo et al. |
| 4,754,381 A | | 6/1988 | Downs |
| 4,757,431 A | | 7/1988 | Cross et al. |
| 4,784,135 A | | 11/1988 | Blum et al. |
| 4,829,262 A | | 5/1989 | Furamoto |
| 4,858,090 A | | 8/1989 | Downs |
| 4,860,172 A | | 8/1989 | Schlager et al. |
| 4,874,361 A | | 10/1989 | Obagi |
| 4,897,771 A | | 1/1990 | Parker |
| 4,930,504 A | | 6/1990 | Diamantopoulos et al. |
| 4,947,305 A | | 8/1990 | Gunter, Jr. |
| 4,950,880 A | | 8/1990 | Hayner |
| 4,974,138 A | | 11/1990 | Negishi |
| 5,057,104 A | | 10/1991 | Chess |
| 5,109,463 A | | 4/1992 | Lee |
| 5,161,526 A | | 11/1992 | Hellwing et al. |
| 5,207,671 A | | 5/1993 | Franken et al. |
| 5,217,455 A | | 6/1993 | Tan |
| 5,226,907 A | | 7/1993 | Tankovich |
| 5,259,380 A | | 11/1993 | Mendes et al. |
| 5,265,598 A | | 11/1993 | Searfoss et al. |
| 5,282,797 A | | 2/1994 | Chess |
| 5,300,097 A | | 4/1994 | Lerner et al. |
| 5,320,618 A | | 6/1994 | Gustafsson |
| 5,330,517 A | | 7/1994 | Mordon et al. |
| 5,337,741 A | | 8/1994 | Diamond |
| 5,344,418 A | * | 9/1994 | Ghaffari ........................ 606/9 |
| 5,344,434 A | | 9/1994 | Talmore |
| 5,394,307 A | | 2/1995 | Matsuura |
| 5,405,368 A | | 4/1995 | Eckhouse |
| 5,414,600 A | | 5/1995 | Strobl et al. |
| 5,425,728 A | | 6/1995 | Tankovich |
| 5,441,531 A | | 8/1995 | Zarate et al. |
| 5,511,563 A | | 4/1996 | Diamond |
| 5,527,350 A | | 6/1996 | Grove et al. |
| 5,560,699 A | | 10/1996 | Davenport et al. |
| 5,595,568 A | | 1/1997 | Anderson et al. |
| 5,606,798 A | | 3/1997 | Kelman |
| 5,620,478 A | * | 4/1997 | Eckhouse ..................... 606/9 |
| 5,626,631 A | | 5/1997 | Eckhouse |
| 5,683,380 A | * | 11/1997 | Eckhouse et al. .............. 606/9 |
| 5,707,413 A | | 1/1998 | Grove et al. |
| 5,720,772 A | | 2/1998 | Eckhouse |
| 5,735,844 A | | 4/1998 | Anderson et al. |
| 5,843,143 A | | 12/1998 | Whitehurst |
| 5,885,273 A | | 3/1999 | Eckhouse et al. |
| 6,280,438 B1 | * | 8/2001 | Eckhouse et al. .............. 606/9 |

* cited by examiner

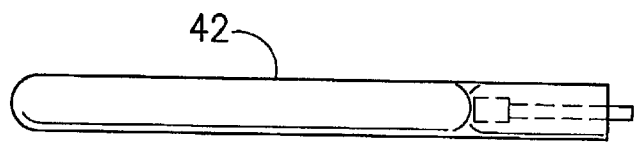
FIG.5
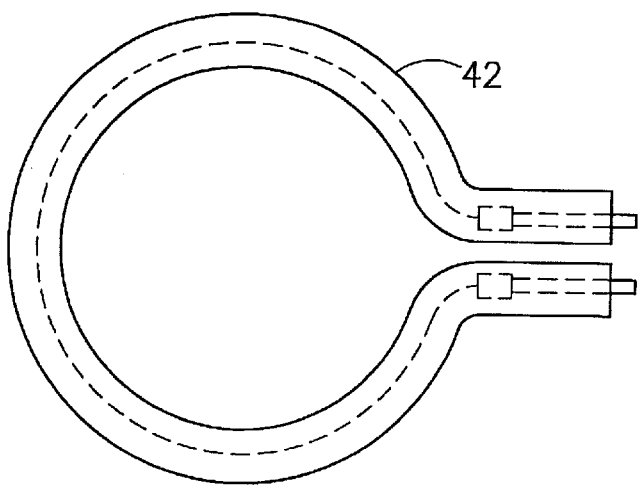
FIG.6
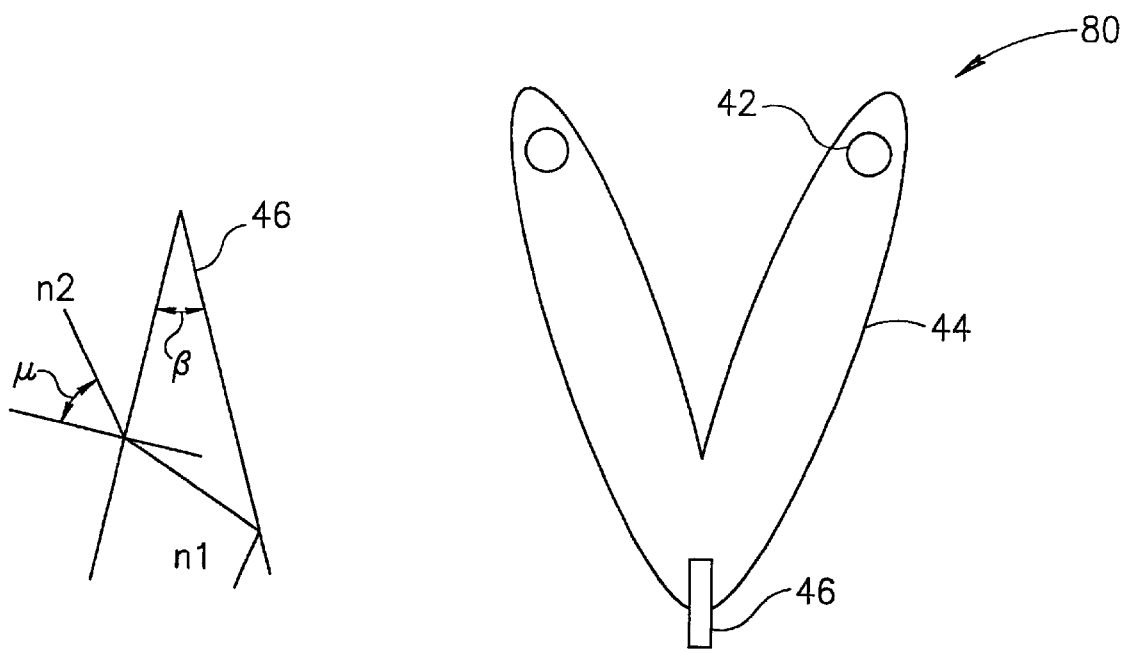
FIG.7
FIG.8

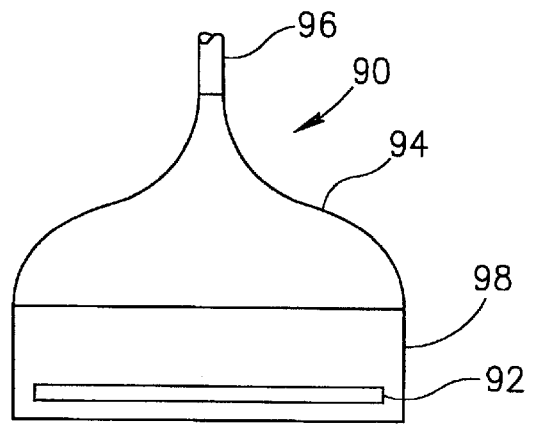
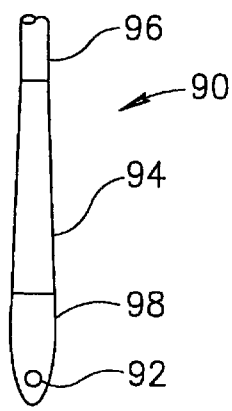
FIG.9　　　FIG.10
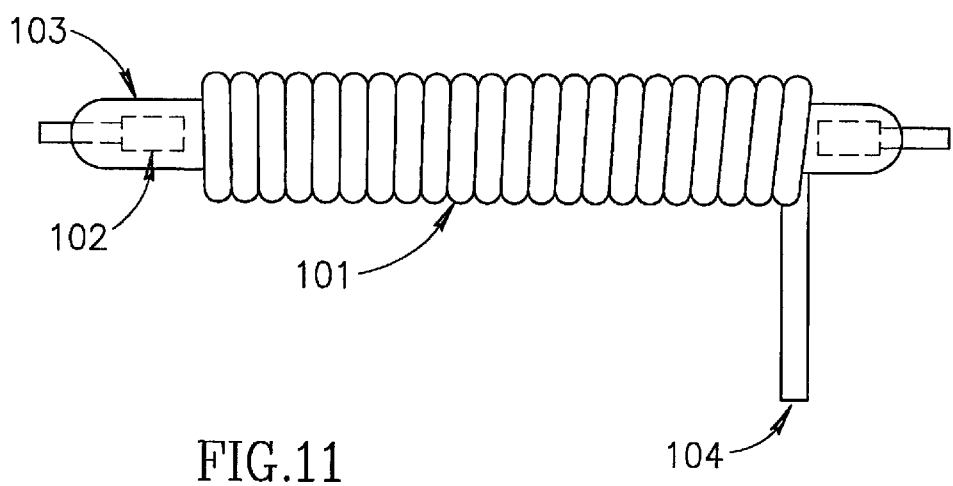
FIG.11
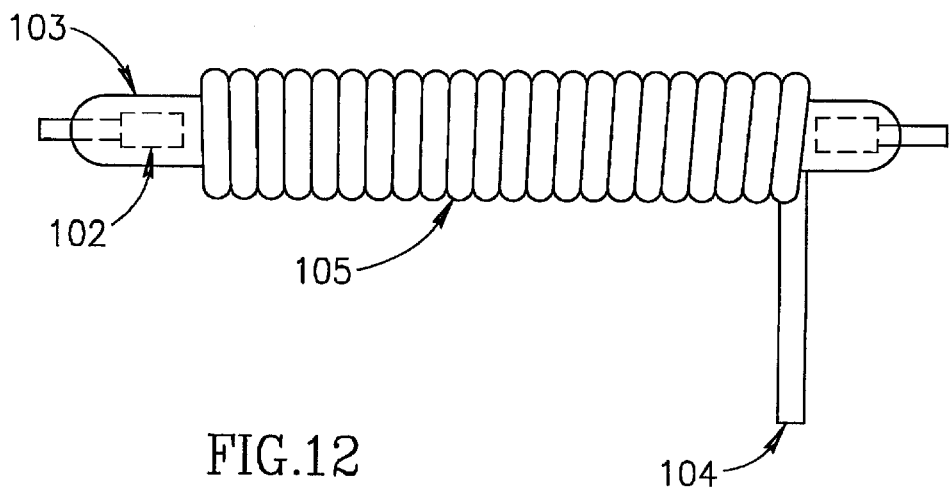
FIG.12

METHOD AND APPARATUS FOR ELECTROMAGNETIC TREATMENT OF THE SKIN, INCLUDING HAIR DEPILATION

RELATED APPLICATIONS

This application is a continuation of U.S. application Ser. No. 08/912,764, filed Aug. 18, 1997 now U.S. Pat. No. 6,280,438, which is a continuation-in-part of U.S. application Ser. No. 08/508,129, filed Jul. 27, 1995, now U.S. Pat. No. 5,720,772, issued on Feb. 24, 1998; which is a continuation in part of U.S. application Ser. No. 08/477,479, filed Jun. 7, 1995, now U.S. Pat. No. 5,620,478, issued on Apr. 15, 1997; which is a continuation of U.S. application Ser. No. 08/473,532, filed Jun. 7, 1995, now U.S. Pat. No. 5,755,751, issued on May 26, 1998; which is a continuation of U.S. application Ser. No. 08/383,509, filed Feb. 3, 1995, now U.S. Pat. No. 5,626,631, issued on May 6, 1997; which is a continuation-in-part of U.S. application Ser. No. 07/964,210, filed Oct. 20, 1992, now U.S. Pat. No. 5,405,368, issued on Apr. 11, 1995; which are incorporated herein by reference. U.S. application Ser. No. 08/912,764 is also a continuation-in-part of U.S. application Ser. No. 08/412,519, filed Mar. 29, 1995, now U.S. Pat. No. 5,683,380, issued on Nov. 4, 1997, which is incorporated herein by reference.

FIELD OF THE INVENTION

The present invention relates generally to the art of electromagnetic skin treatment, including devices and methods for removing hair. The invention relates to a method and apparatus for utilizing a spatially dispersed or extended pulsed light source such as a flashlamp and providing treatment parameters for its use, and also relates to use of devices and methods that utilize electromagnetic energy to kill hair follicles.

BACKGROUND OF THE INVENTION

It is known in the prior art to use electromagnetic radiation in medical applications for therapeutic uses such as treatment of skin disorders. For example, U.S. Pat. No. 4,298,005 to Mutzhas describes a continuous ultraviolet lamp with cosmetic, photobiological, and photochemical applications. A treatment based on using the UV portion of the spectrum and its photochemical interaction with the skin is described. The power delivered to the skin using Mutzhas' lamp is described as 150 W/m$^2$; which does not have a significant effect on skin temperature.

In addition to prior art treatment involving UV light, lasers have been used for dermatological procedures, including Argon lasers, CO$_2$ lasers, Nd(Yag) lasers, Copper vapor lasers, ruby lasers and dye lasers For example, U.S. Pat. No. 4,829,262 to Furumoto, describes a method of constructing a dye laser used in dermatology applications. Two skin conditions which may be treated by laser radiation are external skin irregularities such as local differences in the pigmentation or structure of the skin, and vascular disorders lying deeper under the skin which cause a variety of skin abnormalities including port wine stains, telangiectasias, leg veins and cherry and spider angiomas. Laser treatment of these skin disorders generally includes localized heating of the treatment area by absorption of laser radiation. Heating the skin changes or corrects the skin disorder and causes the full or partial disappearance of the skin abnormality.

Certain external disorders such as pigmented lesions can also be treated by heating the skin very fast to a high enough temperature to evaporate parts of the skin. Deeper-lying vascular disorders are more typically treated by heating the blood to a high enough temperature to cause it to coagulate. The disorder will then eventually disappear. To control the treatment depth a pulsed radiation source is often used. The depth the heat penetrates in the blood vessel is controlled by controlling the pulse width of the radiation source. The adsorption and scattering coefficients of the skin also affect the heat penetration. These coefficients are a function of the constituents of skin and the wavelength of the radiation. Specifically, the absorption coefficient of light in the epidermis and dermis tends to be a slowly varying, monotonically decreasing function of wavelength. Thus, the wavelength of the light should be chosen so that the absorption coefficient is optimized for the particular skin condition and vessel size being treated.

The effectiveness of lasers for applications such as tattoo removal and removal of birth and age marks is diminished because lasers are monochromatic. A laser of a given wavelength may be effectively used to treat a first type of skin pigmentation disorder, but if the specific wavelength of the laser is not absorbed efficiently by skin having a second type of disorder, it will be ineffective for the second type of skin disorder. Also, lasers are usually complicated, expensive to manufacture, large for the amount of power delivered, unreliable and difficult to maintain.

The wavelength of the light also affects vascular disorder treatment because blood content in the vicinity of the vascular disorders varies, and blood content affects the absorption coefficient of the treatment area. Oxyhemoglobin is the main chromophore which controls the optical properties of blood and has strong absorption bands in the visible region. More particularly, the strongest absorption peak of oxyhemoglobin occurs at 418 nm and has a band-width of 60 nm. Two additional absorption peaks with lower absorption coefficients occur at 542 and 577 nm. The total band-width of these two peaks is on the order of 100 nm. Additionally, light in the wavelength range of 500 to 600 nm is desirable for the treatment of blood vessel disorders of the skin since it is absorbed by the blood and penetrates through the skin. Longer wavelengths up to 1000 nm are also effective since they can penetrate deeper into the skin, heat the surrounding tissue and, if the pulse-width is long enough, contribute to heating the blood vessel by thermal conductivity. Also, longer wavelengths are effective for treatment of larger diameter vessels because the lower absorption coefficient is compensated for by the longer path of light in the vessel.

Accordingly, a wide band electromagnetic radiation source that covers the near UV and the visible portion of the spectrum would be desirable for treatment of external skin and vascular disorders. The overall range of wavelengths of the light source should be sufficient to optimize treatment for any of a number of applications. Such a therapeutic electromagnetic radiation device should also be capable of providing an optimal wavelength range within the overall range for the specific disorder being treated. The intensity of the light should be sufficient to cause the required thermal effect by raising the temperature of the treatment area to the required temperature. Also, the pulse-width should be variable over a wide enough range so as to achieve the optimal penetration depth for each application. Therefore, it is desirable to provide a light source having a wide range of wavelengths, which can be selected according to the required skin treatment, with a controlled pulse-width and a high enough energy density for application to the affected area.

Pulsed non-laser type light sources such as linear flashlamps provide these benefits. The intensity of the emitted light can be made high enough to achieve the required thermal effects. The pulse-width can be varied over a wide range so that control of thermal depth penetration can be accomplished. The typical spectrum covers the visible and ultraviolet range and the optical bands most effective for specific applications can be selected, or enhanced using fluorescent materials. Moreover, non-laser type light sources such as flashlamps are much simpler and easier to manufacture than lasers, are significantly less expensive for the same output power and have the potential of being more efficient and more reliable. They have a wide spectral range that can be optimized for a variety of specific skin treatment applications. These sources also have a pulse length that can be varied over a wide range which is critical for the different types of skin treatments.

In addition to being used for treating skin disorders, lasers have been used for invasive medical procedures such as lithotripsy and removal of blood vessel blockage. In such invasive procedures laser light is coupled to optical fibers and delivered through the fiber to the treatment area. In lithotripsy the fiber delivers light from a pulsed laser to a kidney or gallstone and the light interaction with the stone creates a shock wave which pulverizes the stone. To remove blood vessel blockage the light is coupled to the blockage by the fiber and disintegrates the blockage. In either case the shortcomings of lasers discussed above with respect to laser skin treatment are present. Accordingly, a treatment device for lithotripsy and blockage removal utilizing a flashlamp would be desirable.

To effectively treat an area the light from the source must be focussed on the treatment area. Coupling pulsed laser light into optical fibers in medicine is quite common. The prior art describes coupling isotropic incoherent point sources such as CW lamps into small optical fibers. For example, U.S. Pat. No. 4,757,431, issued Jul. 12, 1988, to Cross, et al. discloses a method for focusing incoherent point sources with small filaments or an arc lamp with an electrode separation of 2 mm into a small area. Point (or small) sources are relatively easy to focus without large losses in energy because of the small size of the source. Also, U.S. Pat. No. 4,022,534, issued May 10, 1977, to Kishner discloses light produced by a flash tube and the collection of only a small portion of the light emitted by the tube into an optical fiber.

However, the large dimension of an extended source such as a flashlamp makes it difficult to focus large fractions of its energy into small area. Coupling into optical fibers is even more difficult since not only must a high energy density be achieved, but the angular distribution of the light has to be such that trapping in the optical fiber can be accomplished. Thus, it is desirable to have a system for coupling the output of a high intensity, extended, pulsed light source into an optical fiber.

Hair can be removed permanently for cosmetic reasons by various methods, for example, by heating the hair and the hair follicle to a high enough temperature that results in their coagulation. It is known that blood is coagulated when heated to temperatures of the order of 70° C. Similarly, heating of the epidermis, the hair and the hair follicle to temperatures of the same order of magnitude will also cause their coagulation and will result in permanent removal of the hair.

One common method of hair removal, often called electrolysis, is based on the use of "electric needles" that are applied to each individual hair. An electrical current is applied to each hair through the needle. The current heats the hair, causes its carbonization and also causes coagulation of the tissue next to the hair and some coagulation of the micro vessels that feed the hair follicle.

While the electrical needle method can remove hair permanently or long term, its use is practically limited because the treatment is painful and the procedure is generally tedious and lengthy.

Light can also be used effectively to remove hair. For example, other prior art methods of hair removal involve the application of pulsed light, generally from coherent sources such as lasers. R. A. Harte, et al., in U.S. Pat. No. 3,693,623, and C. Block, in U.S. Pat. No. 3,834,391, teach to remove hair by coagulating single hair with a light coupled to the individual hair by an optical fiber at the immediate vicinity of the hair. Similarly, R. G. Meyer, in U.S. Pat. No. 3,538,919, removes hair on a hair by hair basis using energy from a pulsed laser. Similar inventions using small fibers are described in U.S. Pat. No. 4,388,924 to H. Weissman, et al. and U.S. Pat. No. 4,617,926 to A. Sutton. Each of these teach to remove hair one hair at a time, and are thus slow and tedious.

U.S. Pat. No. 5,226,907, to N. Tankovich, describes a hair removal method based on the use of a material that coats the hair and hair follicle. The coating material enhances absorption of energy by the follicles, either by matching the frequency of a light source to the absorption frequency of the material, or by photochemical reaction. In either case the light source is a laser. One deficiency of such a method and apparatus is that lasers can be expensive and subject to stringent regulations. Additionally, the coating material must be applied only to the hair follicles, to insure proper hair removal and to prevent damage of other tissue.

Light (electromagnetic) energy used to remove hair must have a fluence such that sufficient energy will be absorbed by the hair and the hair follicle to raise the temperature to the desired value. However, if the light is applied to the surface of the skin other than at the precise location of a hair follicle, the light will also heat the skin to coagulation temperature and induce a burn in the skin.

Accordingly, it is desirable to be able to treat the skin by effectively heating multiple follicles, without burning the surrounding skin. Such a method and apparatus should be able to remove more than one hair at a time, and preferably over a wide area of skin, for example at least two square centimeters. Additionally, the method and apparatus should be capable of using incoherent light.

SUMMARY OF THE INVENTION

According to a first embodiment of the invention a therapeutic treatment device comprises a housing and an incoherent light source, suitably a flashlamp, operable to provide a pulsed light output for treatment, disposed in the housing. The housing has an opening and is suitable for being disposed adjacent a skin treatment area. A reflector is mounted within the housing proximate the light source, and at least one optical filter is mounted proximate the opening in the housing. An iris is mounted coextensively with the opening. Power to the lamp is provided by a variable pulse width forming circuit. Thus, the treatment device provides controlled density, filtered, pulsed light output through an opening in the housing to a skin area for treatment.

According to a second embodiment of the invention a method of treatment with light energy comprises the steps of providing a high power, pulsed light output from a non-laser, incoherent light source and directing the pulsed light output to a treatment area. The pulse width of the light output is controlled and focussed so that the power density of the light is controlled. Also, the light is filtered to control the spectrum of the light.

According to a third embodiment of the invention a coupler comprises an incoherent light source such as a toroidal flashlamp. A reflector is disposed around the incoherent light source and at least one optical fiber or light guide. The fiber has an end disposed within the reflector. This end collects the light from the circular lamp. In a similar coupling configuration fibers may be provided, along with a linear to circular fiber transfer unit disposed to receive light from the light source and provide light to the optical fibers. The reflector has an elliptical cross-section in a plane parallel to the axis of the linear flash tube, and the linear flash tube is located at one focus of the ellipse while the linear to circular transfer unit is located at the other focus of the ellipse.

The invention further includes the method of treating the skin to remove hair from an an area of tissue by producing electromagnetic energy and applying the energy to the skin. At least one pulse of incoherent electromagnetic energy is preferably used. The incoherent electromagnetic energy is then coupled to an area of the surface of the tissue that includes more than one hair follicle.

Additionally, in one alternative embodiment the energy may, but not necessarily, be produced by pulsing a flashlamp to generate a pulse having an energy fluence on the order of 10 to 100 J/cm$^2$. The energy can be coupled through a window in a housing in which the flashlamp is located, by reflecting the energy to the tissue through the window and through a gel located on a surface of the tissue. The window may be brought into contact with the gel. In other alternative embodiments the angular divergence of the electromagnetic energy is controlled, and thus the depth of penetration into the tissue, and the coupling to the hair and to the hair follicles, is also controlled. In another alternative embodiment each step of the method is repeated, but at least two angular divergences are used, thus obtaining at least two depths of penetration.

In other alternative embodiments, electromagnetic energy is filtered. Specifically, in one embodiment the electromagnetic energy is filtered according to the pigmentation level of the tissue to be treated. In another alternative, energy that has a wavelength of less than 550 nm and greater than 1300 nm is filtered. Some or all of such energy can be filtered.

In yet another alternative embodiment, the pulse produced has a width of less than 200 msec, and/or the delay between pulses is on the order of 10 to 100 msec between the pulses. In one embodiment, the surface area of the energy at the tissue is at least two square centimeters.

In accordance with a second aspect of the invention an apparatus for removing hair from an area of tissue that includes more than one hair follicle includes a source of pulsed incoherent electromagnetic energy. The source is located within a housing, and a coupler directs the incoherent electromagnetic energy to the surface of the tissue.

According to an alternative embodiment the source is a flashlamp and a pulse generating circuit that generates pulses of energy that have an energy fluence on the order of 10 to 100 J/cm$^2$. The coupler can include a transparent window and the housing a reflective interior, wherein the energy is reflected to the window. A gel is disposed on the surface of the tissue and the window is in contact with the gel, to couple the energy through the window and gel to the surface of the tissue. In another alternative embodiment the energy provided by the coupler has a range of angular divergences.

In another alternative embodiment at least one band pass electromagnetic filter is disposed between the source and the tissue. The filter can be selected such that the wavelength of the energy that passes through the filter is based on the pigmentation level of the treated tissue. Alternatively, the filters pass energy that has a wavelength of between 550 nm and 1300 nm.

In other embodiments, the source provides pulses having a width of less than 200 msec, and/or delays between pulses on the order of 10 to 100 msec. In another embodiment, the area of the energy at the tissue is at least two square centimeters.

According to a third aspect of the invention, a method of removing hair from an area of tissue that has more than one hair follicle includes producing at least one pulse of electromagnetic energy. A gel on a surface of the tissue cools the tissue, but the gel is not adjacent the hair follicle. The electromagnetic energy is coupled to the surface of the tissue.

In one alternative embodiment, the energy is produced by pulsing a flashlamp, and a pulse having an energy fluence on the order of 10 to 100 J/cm$^2$ is thereby generated. In another embodiment, the flashlamp is located in a housing that includes a transparent window and the energy is reflected through the window and directed through the gel to the tissue. In yet another alternative embodiment, the angular divergence of the electromagnetic energy is selected to determine the depth of penetration into the tissue, and to determine the coupling to the hair and to the hair follicles. Also, each step of the method may be repeated using at least two different angular divergences, whereby at least two depths of penetration are obtained.

In another alternative embodiment, the electromagnetic energy is filtered. The filtering can be done in accordance with the pigmentation level of the treated tissue. Alternatively, filtering may include filtering some or all of the energy that has a wavelength of less than 550 nm and greater than 1300 nm.

In another alternative embodiment pulses produced have a width of less than 200 msec. The delay between pulses may be on the order of 10 to 100 msec. Also, the area of the energy at the tissue can be large, for example more than two square centimeters. The energy may be incoherent, such as that produced by a flashlamp for example, or coherent, such as that produced by a laser, for example.

In accordance with another aspect of the invention, an apparatus for removing hair from an area of tissue that has more than one hair includes a source of pulsed electromagnetic energy. A gel is disposed on the surface of the tissue such that the gel cools the tissue but is not adjacent, and does not cool, the hair follicle. A coupler is disposed between the source and the surface to couple the energy to the surface.

In one alternative embodiment, the source is a pulsed flashlamp that generates pulses having an energy fluence on the order of 10 to 100 J/cm$^2$. In another alternative, the flashlamp is located in a housing that includes a transparent window and a reflective interior. In yet another alternative embodiment the shape of the coupler determines the angular divergence of the electromagnetic energy, which determines the depth of penetration of the energy into the tissue, and determines the coupling to the hair and to the hair follicles. The apparatus may include a band-pass filter disposed between the source and the surface. In one alternative the band-pass filter passes energy having a wavelength of between 550 nm and 1300 nm. The source may be a source of incoherent energy, or a source of coherent energy, such as a laser, for example.

BRIEF DESCRIPTION OF THE DRAWINGS

For a better understanding of the invention, reference is made to the accompanying drawings, in which like numerals designate corresponding elements or sections throughout, and in which:

FIG. 5 is a side view of a toroidal flash tube;

FIG. 6 is a top view of a toroidal flash tube;

FIG. 7 shows the geometry for coupling into a conical section;

FIG. 8 is a cross-sectional view of a coupler for coupling light from a toroidal flash tube into an optical fiber with a flat edge;

FIG. 9 is a front sectional view of a coupler for coupling light from a linear flash tube into a circular fiber bundle;

FIG. 10 is a side sectional view of the coupler of FIG. 9;

FIG. 11 is a front view of a coupler for coupling light from a linear flash tube into an optical fiber;

FIG. 12 is a front view of a coupler for coupling light from a linear flash tube into a doped optical fiber;

DETAILED DESCRIPTION OF THE INVENTION AND THE PREFERRED EMBODIMENTS

Figure 1:
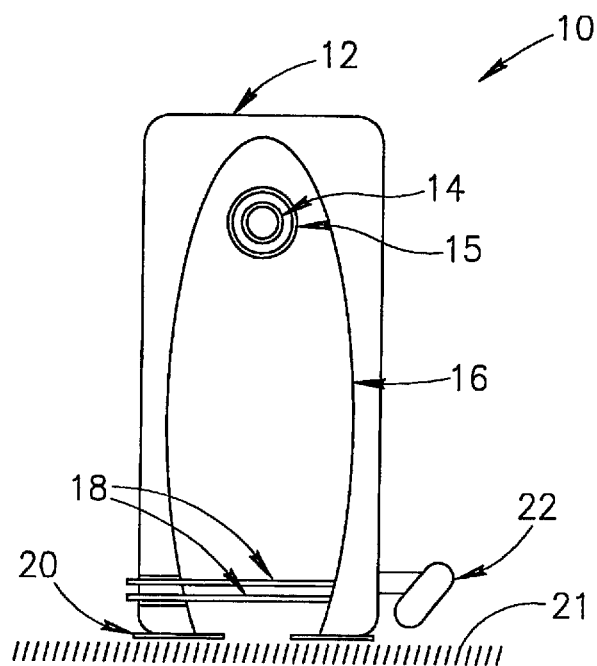
FIG. 1 is a cross-sectional view of an incoherent, pulsed light source skin treatment device.

Before explaining at least one embodiment of the invention in detail it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 2:
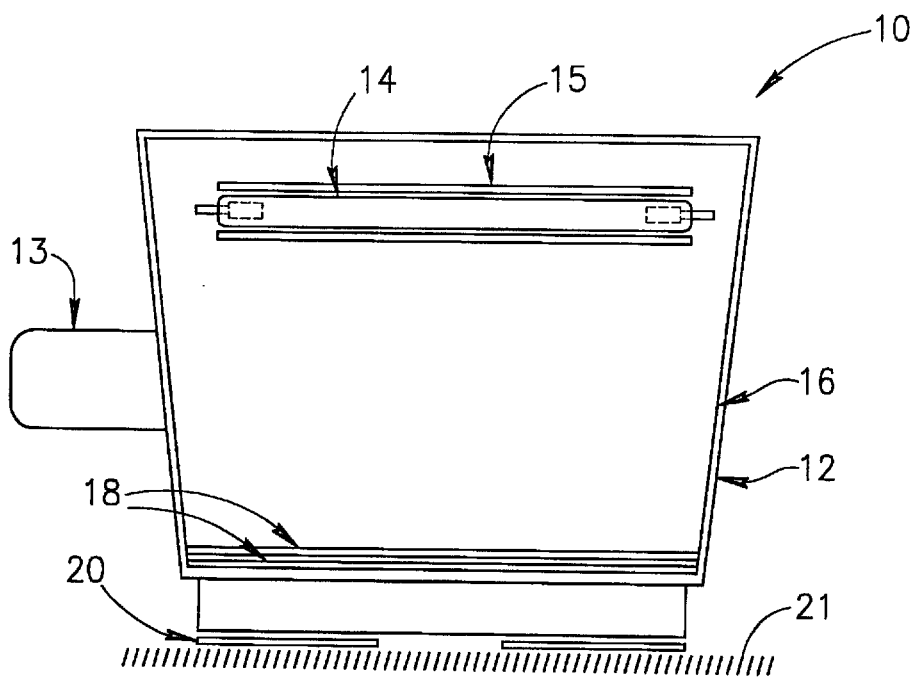
FIG. 2 is a side view of the light source of FIG. 1.

Referring now to FIGS. 1 and 2, cross-sectional and side views of an incoherent, pulsed light source skin treatment device 10 constructed and operated in accordance with the principles of the present invention are shown. The device 10 may be seen to include a housing 12, having an opening therein, a handle 13 (FIG. 2 only), a light source 14 having an outer glass tube 15, an elliptical reflector 16, a set of optical filters 18, an iris 20 and a detector 22 (FIG. 1 only).

Light source 14, which is mounted in housing 12, may be a typical incoherent light source such as a gas filled linear flashlamp Model No. L5568 available from ILC. The spectrum of light emitted by gas filled linear flashlamp 14 depends on current density, type of glass envelope material and gas mixture used in the tube. For large current densities (e.g., 3000 A/$Cm^2$ or more) the spectrum is similar to a black body radiation spectrum. Typically, most of the energy is emitted in the 300 to 1000 nm wavelength range.

To treat a skin (or visible) disorder a required light density on the skin must be delivered. This light density can be achieved with the focusing arrangement shown in FIGS. 1 and 2. FIG. 1 shows a cross-section view of reflector 16, also mounted in housing 12. As shown in FIG. 1, the cross-section of reflector 16 in a plane is perpendicular to the axis of flashlamp 14 is an ellipse. Linear flashlamp 14 is located at one focus of the ellipse and reflector 16 is positioned in such a way that the treatment area of skin 21 is located at the other focus. The arrangement shown is similar to focusing arrangements used with lasers and efficiently couples light from flashlamp 14 to the skin. This arrangement should not, however, be considered limiting. Elliptical reflector 16 may be a metallic reflector, typically polished aluminum which is an easily machinable reflector and has a very high reflectivity in the visible, and the UV range of the spectrum can be used. Other bare or coated metals can also be used for this purpose.

Optical and neutral density filters 18 are mounted in housing 12 near the treatment area and may be moved into the beam or out of the beam to control the spectrum and intensity of the light. Typically, 50 to 100 nm bandwidth filters, as well as low cutoff filters in the visible and ultraviolet portions of the spectrum, are used. In some procedures it is desirable to use most of the spectrum, with only the UV portion being cut off. In other applications, mainly for deeper penetration, it is preferable to use narrower bandwidths. The bandwidth filters and the cutoff filters are readily available commercially.

Glass tube 15 is located coaxially with flashlamp 14 and has fluorescent material deposited on it. Glass tube 15 will typically be used for treatment of coagulation of blood vessels to optimize the energy efficiency of device 10. The fluorescent material can be chosen to absorb the UV portion of the spectrum of flashlamp 14 and generate light in the 500 to 650 nm range that is optimized for absorption in the blood. Similar materials are coated on the inner walls of commercial fluorescent lamps. A typical material used to generate "warm" white light in fluorescent lamps has a conversion efficiency of 80%, has a peak emission wavelength of 570 nm and has a bandwidth of 70 nm and is useful for absorption in blood. The few millisecond decay time of these phosphors is consistent with long pulses that are required for the treatment of blood vessels.

Other shapes or configurations of flashlamp 14 such as circular, helical, short arc and multiple linear flashlamps may be used. Reflector 16 may have other designs such as parabolic or circular reflectors. The light source can also be used without a reflector and the required energy and power density may be achieved by locating light source 14 in close proximity to the treatment area.

Iris 20 is mounted in housing 12 between optical filters 18 and the treatment area and controls the length and the width of the exposed area, i.e. by collimating the output of flashlamp 14. The length of flashlamp 14 controls the maximum length that can be exposed. Typically an 8 cm long (arc length) tube will be used and only the central 5 cm of the tube is exposed. Using the central 5 cm assures a high degree of uniformity of energy density in the exposed skin area. Thus; in this embodiment the iris 20 (also called a collimator) will enable exposure of skin areas of a maximum length of 5 cm. The iris 20 may be closed to provide a minimum exposure length of one millimeter. Similarly, the width of the exposed skin area can be controlled in the range of 1 to 5 mm for a 5 mm wide flashlamp. Larger exposed areas can be easily achieved by using longer flash tubes or multiple tubes, and smaller exposure areas are obtainable with an iris that more completely collimates the beam. The present invention provides a larger exposure area compared to prior art lasers or point sources and is very effective in the coagulation of blood vessels since blood flow interruption over a longer section of the vessel is more effective in coagulating it. The larger area exposed simultaneously also reduces the required procedure time.

Detector 22 (FIG. 1) is mounted outside housing 12 and monitors the light reflected from the skin. Detector 22 combined with optical filters 18 and neutral density filters can be used to achieve a quick estimate of the spectral reflection and absorption coefficients of the skin. This may be carried out at a low energy density level prior to the application of the main treatment pulse. Measurement of the optical properties of the skin prior to the application of the main pulse is useful to determine optimal treatment conditions. As stated above, the wide spectrum of the light emitted from the non-laser type source enables investigation of the skin over a wide spectral range and choice of optimal treatment wavelengths.

In an alternative embodiment, detector 22 or a second detector system may be used for real-time temperature measurements of the skin during its exposure to the pulsed light source. This is useful for skin thermolysis applications with long pulses in which light is absorbed in the epidermis and dermis. When the external portion of the epidermis reaches too high a temperature, permanent scarring of the skin may result. Thus, the temperature of the skin should be measured. This can be realized using infra-red emission of the heated skin, to prevent over exposure.

A typical real-time detector system would measure the infra red emission of the skin at two specific wavelengths by using two detectors and filters. The ratio between the signals of the two detectors can be used to estimate the instantaneous skin temperature. The operation of the pulsed light source can be stopped if a pre-selected skin temperature is reached. This measurement is relatively easy since the temperature threshold for pulsed heating, that may cause skin scarring is on the order of 50° C. or more, which is easily measurable using infra-red emission.

The depth of heat penetration depends on the light absorption and scattering in the different layers of the skin and the thermal properties of the skin. Another important parameter is pulse width. For a pulsed ligh source, the energy of which is absorbed in an infinitesimally thin layer, the depth of heat penetration (d) by thermal conductivity during the pulse can be written as shown in Equation 1:

$$d=4[k\Delta t/Cp]^{1/2} \qquad \text{(Eq. 1)}$$

where k=heat conductivity of the material being illuminated;

$\Delta t$=the pulse-width of the light pulse;

C=the heat capacity of the material;

p=density of the material.

It is clear from Equation 1 that the depth of heat penetration can be controlled by the pulse-width of the light source. Thus, a variation of pulse-width in the range of $10^{-5}$ sec to $10^{-1}$ sec will result in a variation in the thermal penetration by a factor of 100.

Accordingly, the flashlamp 14 provides a pulse width of from $10^{-5}$ sec to $10^{-1}$ sec. For treatment of vascular disorder in which coagulation of blood vessels in the skin is the objective the pulse length is chosen to uniformly heat as much of the entire thickness of the vessel as possible to achieve efficient coagulation. Typical blood vessels that need to be treated in the skin have thicknesses in the range of 0.5 mm. Thus, the optimal pulse-width, taking into account the thermal properties of blood, is on the order of 100 msec. If shorter pulses are used, heat will still be conducted through the blood to cause coagulation, however, the instantaneous temperature of part of the blood in the vessel and surrounding tissue will be higher than the temperature required for coagulation and may cause unwanted damage.

For treatment of external skin disorders in which evaporation of the skin is the objective, a very short pulse-width is used to provide for very shallow thermal penetration of the skin. For example, a $10^{-5}$ sec pulse will penetrate (by thermal conductivity) a depth of the order of only 5 microns into the skin. Thus, only a thin layer of skin is heated, and a very high, instantaneous temperature is obtained so that the external mark on the skin is evaporated.

Figure 3:
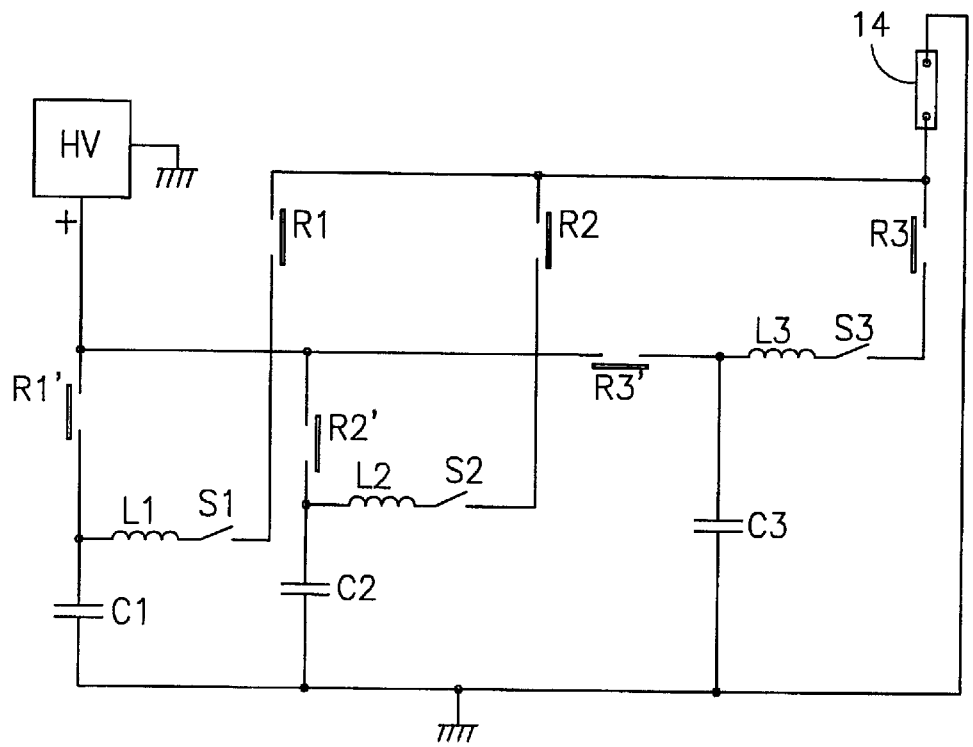
FIG. 3 is a schematic diagram of a pulse forming network with a variable pulse width for use with the skin treatment device of FIGS. 1 and 2.

FIG. 3 shows a variable pulse-width pulse forming circuit comprised of a plurality of individual pulse forming networks (PFN's) that create the variation in pulse widths of flashlamp 14. The light pulse full width at half maximum (FWHM) of a flashlamp driven by a single element PFN with capacitance C and inductance L is approximately equal to:

$$\Delta t=2[LC]^{1/2} \qquad \text{(Eq. 2)}$$

Flashlamp 14 may be driven by three different PFN's, as shown in FIG. 3. The relay contacts R1', R2' and R3' are used to select among three capacitors C1, C2 and C3 that are charged by the high voltage power supply. Relays R1, R2 and R3 are used to select the PFN that will be connected to flashlamp 14. The high voltage switches S1, S2 and S3 are used to discharge the energy stored in the capacitor of the PFN into flashlamp 14. In one embodiment L1, L2 and L3 have values of 100 mH, 1 mH and 5 mH, respectively, and C1, C2 and C3 have values of 100 mF, 1 mF and 10 mF, respectively.

In addition to the possibility of firing each PFN separately, which generates the basic variability in pulse-width, additional variation can be achieved by firing PFN's sequentially. If, for example, two PFN's having pulse-width Δt1 and Δt2 are fired, so that the second PFN is fired after the first pulse has decayed to half of its amplitude, then an effective light pulse-width of this operation of the system will be given by the relation: Δt=Δt1+Δt2.

The charging power supply typical has a voltage range of 500 V to 5 kV. The relays should therefore be high voltage relays that can isolate these voltages reliably. The switches S are capable of carrying the current of flashlamp 14 and to isolate the reverse high voltage generated if the PFNs are sequentially fired. Solid-state switches, vacuum switches or gas switches can be used for this purpose.

A simmer power supply (not shown in FIG. 3) may be used to keep the flashlamp in a low current conducting mode. Other configurations can be used to achieve pulse-width variation, such as the use of a single PFN and a crowbar switch, or use of a switch with closing and opening capabilities.

Typically, for operation of flashlamp 14 with an electrical pulse-width of 1 to 10 msec, a linear electrical energy density input of 100 to 300 J/cm can be used. An energy density of 30 to 100 $J/cm^2$ can be achieved on the skin for a typical flashlamp bore diameter of 5 mm. The use of a 500 to 650 nm bandwidth transmits 20% of the incident energy. Thus, energy densities on the skin of 6 to 20 $J/cm^2$ are achieved. The incorporation of the fluorescent material will further extend the output radiation in the desired range, enabling the same exposure of the skin with a lower energy input into flashlamp 14.

Pulse laser skin treatment shows that energy densities in the range of 0.5 to 10 $J/cm^2$ with pulse-widths in the range of 0.5 msec are generally effective for treating vascular related skin disorders. This range of parameters falls in the range of operation of pulsed non-laser type light sources such as the linear flashlamp. A few steps of neutral density glass filters 18 can also be used to control the energy density on the skin.

For external disorders a typical pulse-width of 5 microsecond is used. A 20 J/cm electrical energy density input into a 5 mm bore flashlamp results in an energy density on the skin of 10 $J/cm^2$. Cutting off the hard UV portion of the spectrum results in 90% energy transmission, or skin exposure to an energy density of close to 10 $J/cm^2$. This energy density is high enough to evaporate external marks on the skin.

Device 10 can be provided as two units: a lightweight unit held by a physician using handle 13, with the hand-held unit containing flashlamp 14, filters 18 and iris 20 that together control the spectrum and the size of the exposed area and the detectors that measure the reflectivity and the instantaneous skin temperature. The power supply, the PFN's and the electrical controls are contained in a separate box (not shown) that is connected to the hand-held unit via a flexible cable. This enables ease of operation and easy access to the areas of the skin that need to be treated.

The invention has thus far been described in conjunction with skin treatment. However, using a flashlamp rather than a laser in invasive treatments provides advantages as well. Procedures such as lithotripsy or removal of blood vessel blockage may be performed with a flashlamp. Such a device may be similar to that shown in FIGS. 1 and 2, and may use the electronics of FIG. 3 to produce the flash. However, to properly couple the light to an optical fiber a number of couplers 40, 80 and 90 are shown in FIGS. 4 and 8–10, respectively.

Coupler 40 includes an optical source of high intensity incoherent and isotropic pulsed light such as a linear flash tube 42, a light reflector 44 which delivers the light energy to an optical fiber 46. The latter has a generally conical edge in the embodiment of FIG. 4. Optical fiber 46 transfers the light from light collection system 44 to the treatment area. In general, coupler 40 couples pulsed light from a flash tube into an optical fiber and has applications in medical, industrial and domestic areas.

For example, coupler 40 may be used in material processing to rapidly heat or ablate a portion of a material being processed, or to induce a photo-chemical process. Alternatively, coupler 40 may be used in a photography application to provide a flash for picture taking. Using such a coupler would allow the flash bulb to be located inside the camera, with the light transmitted to outside the camera using an optical fiber. As one skilled in the art should recognize coupler 40 allows the use of incoherent light in many applications that coherent or incoherent light has been used in the past.

To provide for coupling the light to an optical fiber, flash tube 42 has a toroidal shape, shown in FIGS. 5 and 6, and is disposed inside reflector 44. In addition to the toroidal shape other shapes, such as a continuous helix, may be used for flash tube 42. However, a helical tube is more difficult to manufacture than a toroidal tube. Referring now to FIG. 6, flash tube 42 is generally in the shape of a tours, but is not a perfect tours since the electrodes located at the end of the tours have to be connected to the power source. This does not create a significant disturbance in the circular shape of flash tube 42, since the connection to the electrodes can be made quite small.

Reflector 44 collects and concentrates the light, and has a cross-section of substantially an ellipse, in a plane perpendicular to the minor axis of the toroidal flash tube 42. The major axis of this ellipse preferably forms a small angle with the major axis of toroidal lamp 42. The exact value of the angle between the ellipse axis and the main axis of lamp 42 depends on the Numerical Aperture (NA) of the optical fiber. The toroidal flash tube is positioned so that its minor axis coincides with the focus of the ellipse. The other focus of the ellipse is at the edge of optical fiber 46. Reflector 44 may be machined from metal with the inner surfaces polished for good reflectivity. Aluminum is a very good reflector with high reflectivity in the visible and ultraviolet wavelengths, and it may be used for this purpose. The reflector can be machined in one piece and then cut along a surface perpendicular to the main axis of the device. This will enable integration of the toroidal flash tube into the device.

Figure 4:
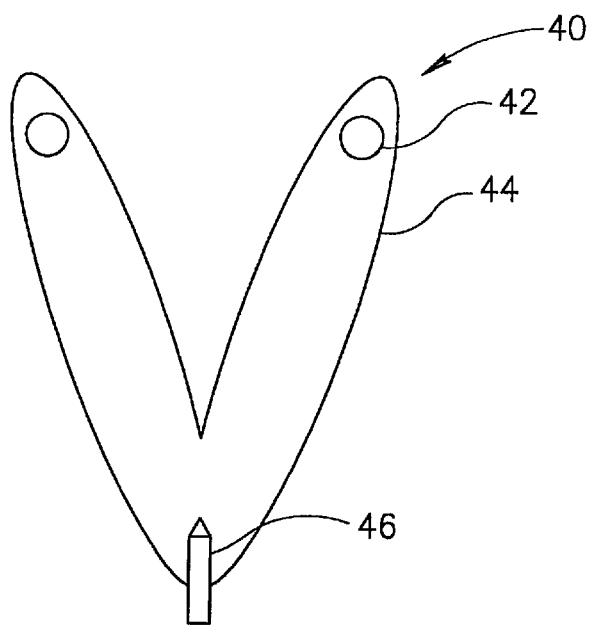
FIG. 4 is a cross-sectional view of a coupler for coupling light from a toroidal flash tube into an optical fiber with a conical edge.

As shown in FIG. 4, the edge of optical fiber 46 is a cone with a small opening angle, so that the total area of the fiber exposed to the light from the flash tube is increased. Referring now to FIG. 7 the geometry for coupling light into a conical tip is shown. It is assumed here that the light comes from a region in space with a refractive index of n and that the conical section of the fiber (as well as the rest of the fiber core) has a refractive index of n1.

Not all the light rays hitting the cone are trapped in it. For light rays that propagate in a plane that contains the major axis of the system, a condition can be derived for the angle of a ray that will be trapped and absorbed in the fiber. This condition is shown in Equation 3.

$$\sin(\mu_{criti}) = \cos(\beta) - [n_1^2/n_2^2 - 1]^{1/2} \sin(\beta) \qquad (\text{Eq. 3})$$

Light will be trapped in the conical portion of the optical fiber if the incidence angle $\mu$ is larger than $\mu_{criti}$ calculated from Equation 3. Trapping is possible only if n1>n2. If the medium outside of the fiber is air, $n_2=1$.

Not all of the light trapped in the conical section of the fiber will also be trapped in the straight portion of the fiber if a fiber with a core and a cladding is used. If a fiber with a core and no cladding is used (air cladding), then all the rays captured in the conical section of the fiber will also be trapped in the straight section of the fiber.

The configuration shown in FIG. 4 can also be used with a fluid filling the volume between the reflector and the optical fiber. A very convenient fluid for this purpose may be water. Water is also very effective in cooling the flashlamp if high repetition rate pulses are used. The presence of a fluid reduces the losses that are associated with glass to air transitions, such as the transition between the flashlamp envelope material and air. If a fluid is used in the reflector volume, then its refractive index can be chosen such that all the rays trapped in the conical section are also trapped in the fiber, even if core/cladding fibers are used.

Another way of configuring the fiber in the reflector is by using a fiber with a flat edge. This configuration is shown in FIG. 8 and has trapping efficiency very close to the trapping efficiency of the conical edge. Many other shapes of the fiber edge, such as spherical shapes, can also be used. The configuration of the fiber edge also has an effect on the distribution of the light on the exit side of the fiber and it can be chosen in accordance with the specific application of the device.

The device may be used with a variety of optical fibers. Single, or a small number of millimeter or sub-millimeter diameter fibers, will typically be used in invasive medical applications. In other applications, particularly in industrial and domestic applications, it may be preferable to use a fiber having a larger diameter, or a larger bundle of fibers, or a light guide.

According to one embodiment flexible or rigid light guides are used to couple the light to the treatment area. Flexible light guides made from a bundle of quartz or other glass fibers that are fused together by heat at the edge of the bundles. The bundles may be circular, rectangular, or any other useful shape. Rigid light guides may be made from quartz, acrylic, glass, or other materials having a high degree of transparency. The material is generally highly polished on all sides.

A typical cross section of a circular light guide useful for therapeutic treatment is one mm to ten mm in diameter. Alternatively, a rectangular light guide may be used having typical dimensions of 3 mm by 10 mm to 30 mm by 100 mm. In either case the length may be 20 to 300 mm, or as needed for the specific application.

According to another alternative embodiment a rectangular light guide is used to more efficiently couple the light. The rectangular light guide is chosen to have a shape that matches a rectangular linear flashlamp and to match the shape of the vessel being treated.

The light guides described above may be used in another alternative embodiment to control the spectrum of light delivered to the treatment area. Spectral control can be achieved by making the light guide from a material that had an absorbing dye dissolved therein. Thus, light transmitted by the light guide will have a spectrum in as determined by the absorbing dye. Alternatively, a flat, discrete filter may be added to one end (preferably the input end) of the light guide. Both of these filters are absorbing filters. The inventors have found that absorbing filters produced by Schott, having Model Nos. OG515, OG550, OG570, and OG590 have suitable characteristics.

Additionally, interference filters or reflective coatings on the light guide may be used by applying a proper optical coating to the light guide. Again, a single discrete interference filter could also be used. Additionally, combinations of the various filters described herein, or other filters, may be used. The use of the filters described here may render the use of the filters described earlier with reference to FIG. 1 redundant.

An alternative embodiment entails the use of application specific light guides. In this way the spectra of light for various treatments can be easily controlled. According to this alternative each type of treatment will be performed with a specific light guide.

The optical properties of the light guide will be chosen to optimize the particular treatment. The wavelengths below are particularly useful for the respective treatments:

arteries less than 0.1 mm in diameter—520–650 nm veins less than 0.1 mm in diameter—520–700 nm vessels between 0.1 and 1.0 mm in diameter—550–1000 nm larger vessels—600–1000 nm In each case if the skin is darker (higher pigmentation) longer wavelengths on the lower cut-off portion of the spectrum should be used.

Multiple spectra may be used for optimal penetration. This may be accomplished by illuminating with a few pulses, each having a different spectrum. For example, the first pulse can have a spectrum that is highly absorbed in blood. This pulse will coagulate the blood, thereby changing the optical properties of the blood, making it more absorbing in another wavelength range (preferably longer). A second pulse will be more efficiently absorbed since the blood absorbs energy of a greater wavelength range. This principle may be used with lasers or other light sources as well.

In addition to the features of the light guides discussed above, a light guide is used, in one alternative embodiment, to control the angular distribution of the light rays impinging on the skin. Light that impinges on the skin at large angles (relative to the perpendicular) will not penetrate very deeply into the tissue. Conversely, light that impinges perpendicularly to the skin will have a deeper penetration. Thus, it is desirable to provide a distribution of light rays that has a relatively wide angular divergence when the treatment requires shallow penetration. Alternatively, a narrow divergence is preferable for treatment requiring deep penetration is desired. Some treatment might require both shallow and deep penetration.

Figures 15, 16:
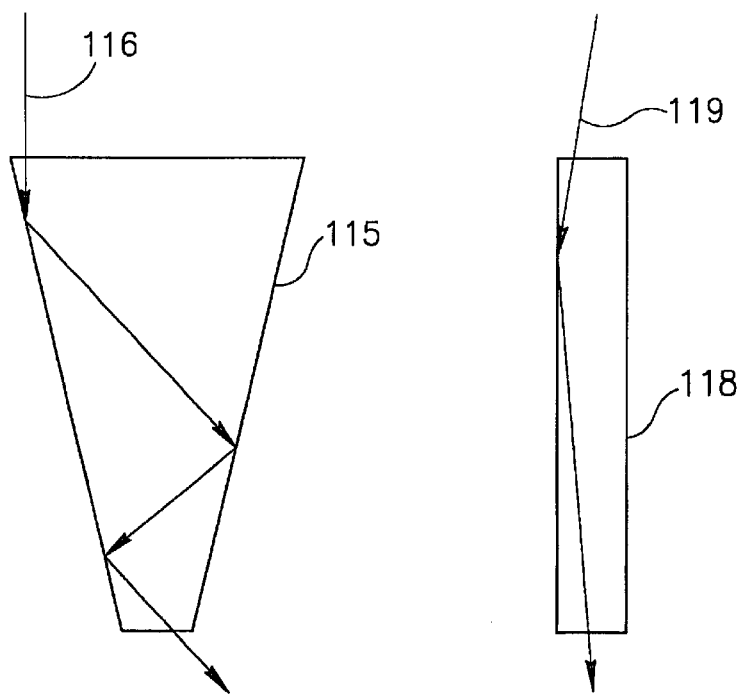
FIG. 15 shows a light guide providing a large angular divergence.
FIG. 16 shows a light guide providing a narrow angular divergence.

FIG. 15 shows a light guide 115 having an exit beam with a greater angular divergence than that of the entrance beam. As shown in FIG. 15, a beam 116 enters light guide 115 at a small angle, relative to the axis of light guide 115. When beam 501 exits light guide 115, the angle, relative to the axis, is much greater. The tapered shape of light guide 115 enhances this divergence.

FIG. 16 shows a straight light guide 118 that maintains the angular distribution of the rays of light that enter into it. A beam 119 is shown entering and exiting light guide 118 with the same angle, relative to the axis of coupler 601. Alternate use of both light guides 115 and 118 can achieve the narrow and deep penetration discussed above. Alternatively, the user can select the type of coupler according to the depth of penetration needed for the treatment being performed.

FIGS. 9 and 10 show a coupler 90 for coupling a linear flash tube 92 through a linear to circular fiber transfer unit 94 to a fiber bundle 96. A reflector 98 has an elliptical cross-section, shown in FIG. 10, in a plane parallel to the axis of linear flash tube 92 in this embodiment. Tube 92 is located on one focus of the ellipse while the linear side of linear to circular bundle converter is located at the other focus of the ellipse. This configuration is relatively simple to manufacture and commercially available linear to circular converters such as 25-004-4 available from General Fiber Optics may be used. This configuration is particularly useful for larger exposure areas of the fiber, or for flash illumination purposes.

The energy and power densities that can be achieved by this invention are high enough to get the desired effects in surface treatment or medical applications. For the embodiment shown in FIG. 4 the total energy and power densities can be estimated as follows. For a typical toroidal lamp with a 4 mm bore diameter and a major diameter of 3.3 cm an electrical linear energy density input of 10 J/cm into the lamp can be used with a $5\mu$ sec pulse width. The light output of the lamp will be 5 to 6 J/cm for optimal electrical operating conditions. For the reflector shown in FIG. 4, 50% of the light generated in the lamp will reach the lower focus. Thus, a total energy flux on the focus of 25 to 30 J may be obtained. For embodiments shown in FIG. 4 or FIG. 8 the total cross-section area of reflector at the focal plane has a cross-section of 0.8 $cm^2$. Energy densities on the order of 30 to 40 $J/cm^2$ at the entrance to the fiber should be attained with this cross-section. This corresponds to power densities of 5 to 10 $MW/cm^2$, which are the typical power densities used in medical or material processing applications.

For longer pulses, higher linear electrical energy densities into the lamp can be used. For a 1 msec pulse to the flash tube a linear electrical energy density of 100 J/cm can be used. The corresponding energy density at the focal area would be up to 300 $J/cm^2$. Such energy densities are very effective in industrial cleaning and processing applications as well as in medical applications.

Alternative embodiments for coupling the optical fiber to an extended light source such as a linear flashlamp are shown in FIGS. 11 and 12. In the embodiment of FIG. 11 an optical fiber 101 is wound around a lamp 102 and a lamp envelope 103. Some of the light that is produced by the light source is coupled into the fiber. If the light rays are propagating in the direction that is trapped by the fiber then this light will propagate in the fiber and it can be used at a fiber output 104. One limitation of this configuration is the fact that most of the light emitted by lamp 103 travels in a direction perpendicular to the surface of lamp 103 and cannot be trapped in fiber 101.

The embodiment shown in FIG. 12 overcomes this problem. A doped optical fiber 105 is wound around lamp 102 and envelope 103, rather than an undoped fiber such as fiber 101 of FIG. 11. The dopant is a fluorescent material which is excited by the radiation emanating from lamp 102 and radiates light inside the fiber. This light is radiated omnidirectionally and the part of it that is within the critical angle of fiber 105 is trapped and propagates through the fiber and can be used at fiber output 104. The angle of light that is trapped in the fiber is the critical angle of the material from which the optical fiber or optical wave guide is made. For a fiber (or optical wave guide) in air this angle is given by $\sin \alpha = 1/n$.

Typically for glass or other transparent materials n=1.5 and $\alpha$=41.8°. This corresponds to a trapping efficiency of more than 10% of the light emitted by fluorescence inside the fiber. If we assume a 50% efficiency of the fluorescence process we find out that more than 5% of the light produced by the lamp is trapped and propagated down the fiber. For example, a 4" lamp with a linear electrical energy input of 300 J/inch and 50% electrical to light conversion efficiency would couple 2.5% of its electrical energy into the fiber. This corresponds, for the 4" lamp case to a total light energy of 30 J of light. This embodiment has the additional advantage of transferring the wavelength emitted by the lamp to a wavelength that may be more useful in some of the therapeutic or processing applications mentioned before. Thus, fluorescent material doped in the fiber can be chosen in accordance with an emission wavelength determined by the specific application of the device.

One alternative embodiment includes the use of a gel to couple the light to the skin. This alternative reduces heating of the outer layer of the skin (the epidermis and upper layers of the dermis). The gel is preferably a high viscosity water based gel and is applied to the skin before treatment, although other gels that are not necessarily water based may be used. A gel having a relatively high heat capacity and thermal conductivity, such as a water based gel, is preferable to enable cooling of the outer skin (the epidermis in particular). Transparency is also desirable because during treatment light passes through the transparent gel and reaches the skin.

Figure 13:
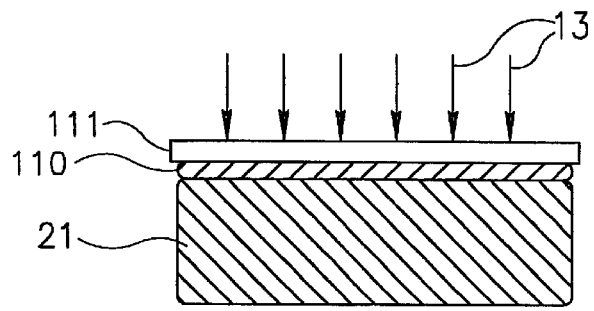
FIG. 13 is a schematic configuration of a gel skin interface with a transparent plate.

Referring now to FIG. 13, a gel 110 is applied to the skin 21 prior to the treatment. A flat layer of gel on top of the skin is used since irregularities in the upper layer of the gel through which the light passes may cause scattering of the light and reduce its penetration into the skin. In order to achieve this flatness a solid, transparent, flat piece 111 may be applied on top of the skin. The configuration is shown schematically in FIG. 13. The transparent plate can be made out of glass or other transparent materials. Either the flashlamp housing or the light guides discussed above may be placed in direct contact with the transparent plate.

Figure 14:
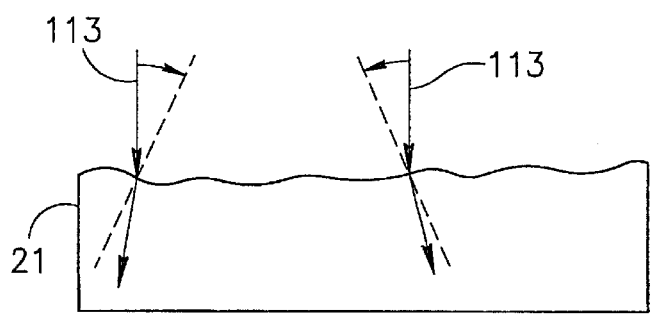
FIG. 14 shows an angular distribution of photons penetrating without using a gel.

The configuration of FIG. 13 has the advantage of reducing the scattering of light (represented by arrows 113) that enters into the skin due to irregularities in the surface of the skin. The skin has an index of refraction that is larger than that of the air. As a result, any photon that impinges on the air skin interface is deflected if it does not hit the skin at an incidence angle of 0°. Since the surface of the skin is irregular the angular distribution of the skin increases. This is shown schematically in FIG. 14.

The use of gel addresses this problem since the gel can fill irregular voids that are created by the skin structure. The transparent plate that covers the gel and the gel itself will preferably have an index of refraction that is close to that of the skin. This is relatively easy since the index of refraction of the skin is of the order of 1.4 in the visible and the near infrared. Most glasses and transparent plastics have indices of refraction that are of the order of 1.5 which is close enough. The index of refraction of water is of the order of 1.34 in this range. Water based gels will have similar indices of refraction. The index can be increased by proper additives. The plate and gel thus act as a flat surface for the light to impinge upon. Because the gel and plate have an index of refraction close to that of the skin there is very little scattering at the gel-plate and gel skin interfaces.

The use of a gel has been experimentally successful in the treatment of leg veins and other benign vascular lesions of the skin. The treatments were carried out with the flashlamp described above. However, in alternative embodiments a different incoherent source, or a coherent source, may be used.

During operation light is typically applied to the skin in a sequence of three pulses with short delays between the pulses. This mode of operation is used in order to take advantage of the faster cooling of the superficial, thin (less than 0.1 mm thick) epidermis compared to the larger and deeper vessels (typical of leg veins. The gel in contact with the skin cools the epidermis during the waiting period between the pulses. This cooling reduces significantly the damage to the epidermis.

In accordance with the invention, light is applied to the treated area in either a long pulse or in a sequence of pulses separated by a delay. The delay and/or pulse length is preferably controlled by the operator to provide enough heat to accomplish the desired treatment but not enough heat to damage the skin.

This concept was tested with large and deep vessels (of the order of 2 mm in diameter and 2 mm deep). A thin layer of commercial water based ultrasound gel (1 to 2 mm thick, "Aqua clear" gel made by Parker USA) was applied on the skin. A 1 mm thin glass window was used to generate a flat layer of the gel. The light from the device passed through the thin glass and the gel and into the skin. Care was taken to assure than no air bubbles exist in the gel. This configuration was tested with photon fluences of 30 to 50 $J/cm^2$. Coagulation and clearance of the vessels was obtained without causing damage to the skin. This is contrary to similar trials in which gel was not used and in which fluences of 20 J/cm: with the same pulse structure caused burns of the skin.

The epidermis has a thickness of approximately 0.1 mm and a cooling time of about 5 msec. Thus, to avoid burning delays greater than 5 msec are used.

In another alternative embodiment the spectrum of the light used for treatment is controlled by controlling the voltage and/or current applied to the flashlamp. As is well known in the art, the spectrum of light produced by a flashlamp is dependent on the voltage and current provided to the flashlamp. According to this embodiment the input voltage and current is selected to provide a desired treatment spectrum. The appropriate voltage and currents may be determined experimentally for each flashlamp used.

Figure 17:
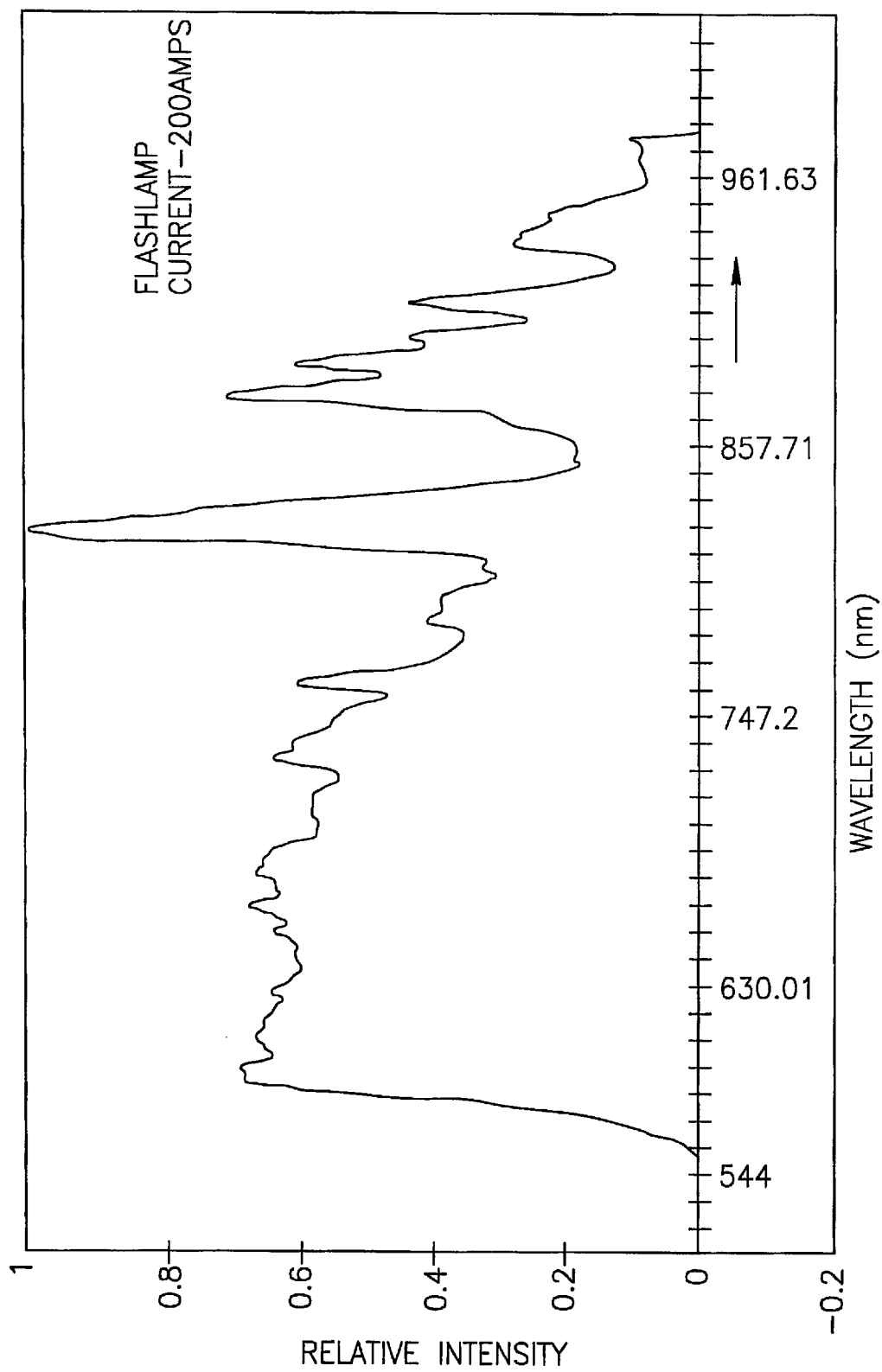
FIG. 17 shows a spectra produced with a flashlamp current of 200 amps.
Figure 18:
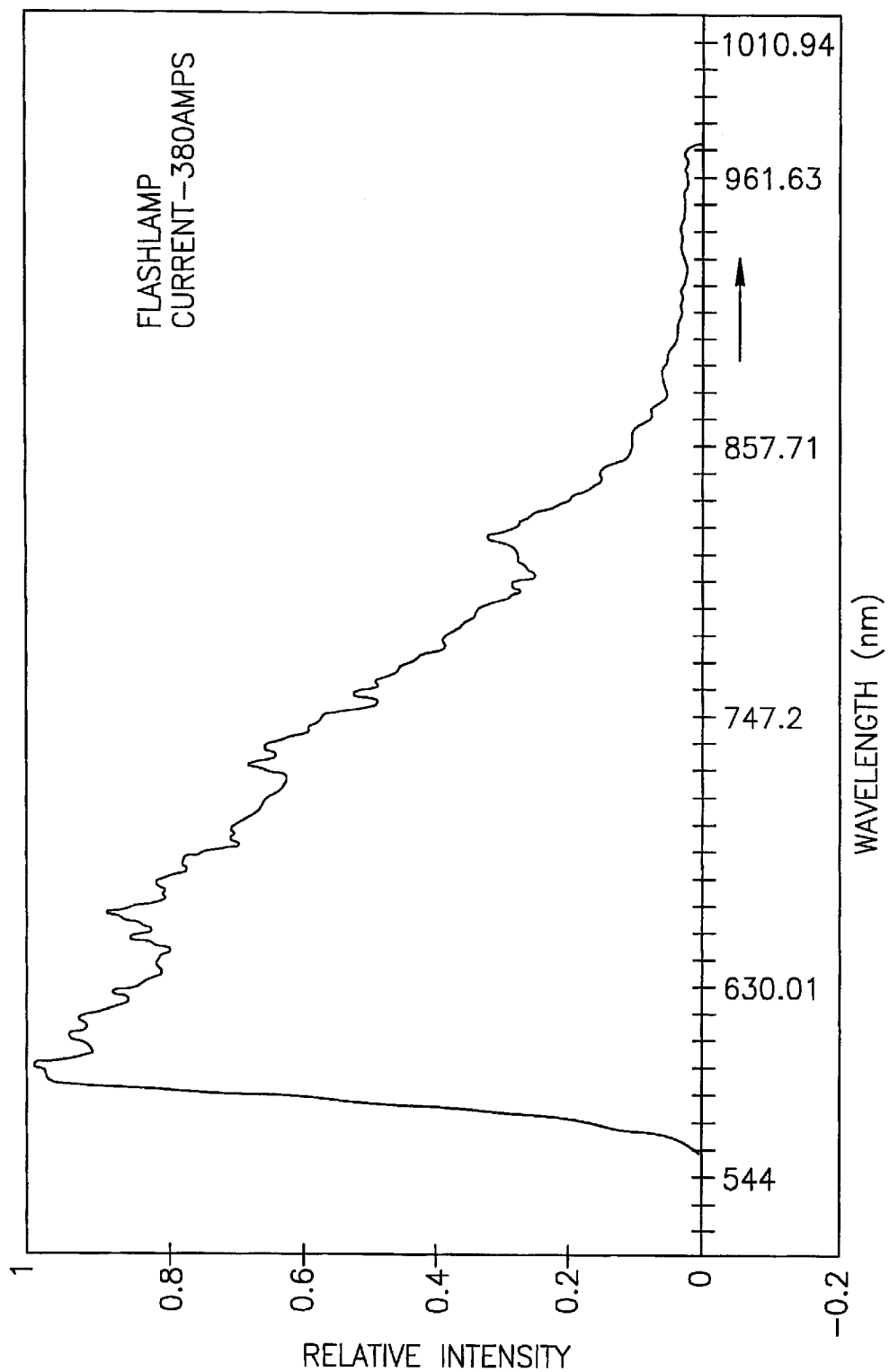
FIG. 18 shows a spectra produced with a flashlamp current of 200 amps.

For example, a flashlamp current of 200 amps produced the spectra shown in FIG. 17. Similarly, the spectra of FIG. 18 was produced using a flashlamp current of 380 amps. The spectra of FIG. 17 shows a significant enhancement in the wavelength range of 800–1000 nm. Such a spectra is particularly useful for treatment of large vessels.

The different currents and voltages used to control the output spectra may be obtained using a group or bank of capacitors that are capable of being connected in either series or parallel as part of the power source for the flashlamp. A series connection will provide a relatively high voltage and high current, thereby producing a spectra having energy in a shorter wavelength, such as 500–600 nm. Such a series connection will be more appropriate for generating shorter pulses (1 to 10 msec, e.g.) useful for treatment of smaller vessels.

A parallel connection provides a lower current and voltage, and thus produces an output spectra of a longer wavelength, such as 700–1000 nm. Such a spectra is more appropriate for treatment of larger vessels and is suitable for producing longer pulses (in the range of 10–50 msec, e.g.). The selection of series or parallel connections may be done using a relay or sets of relays.

Figure 19:
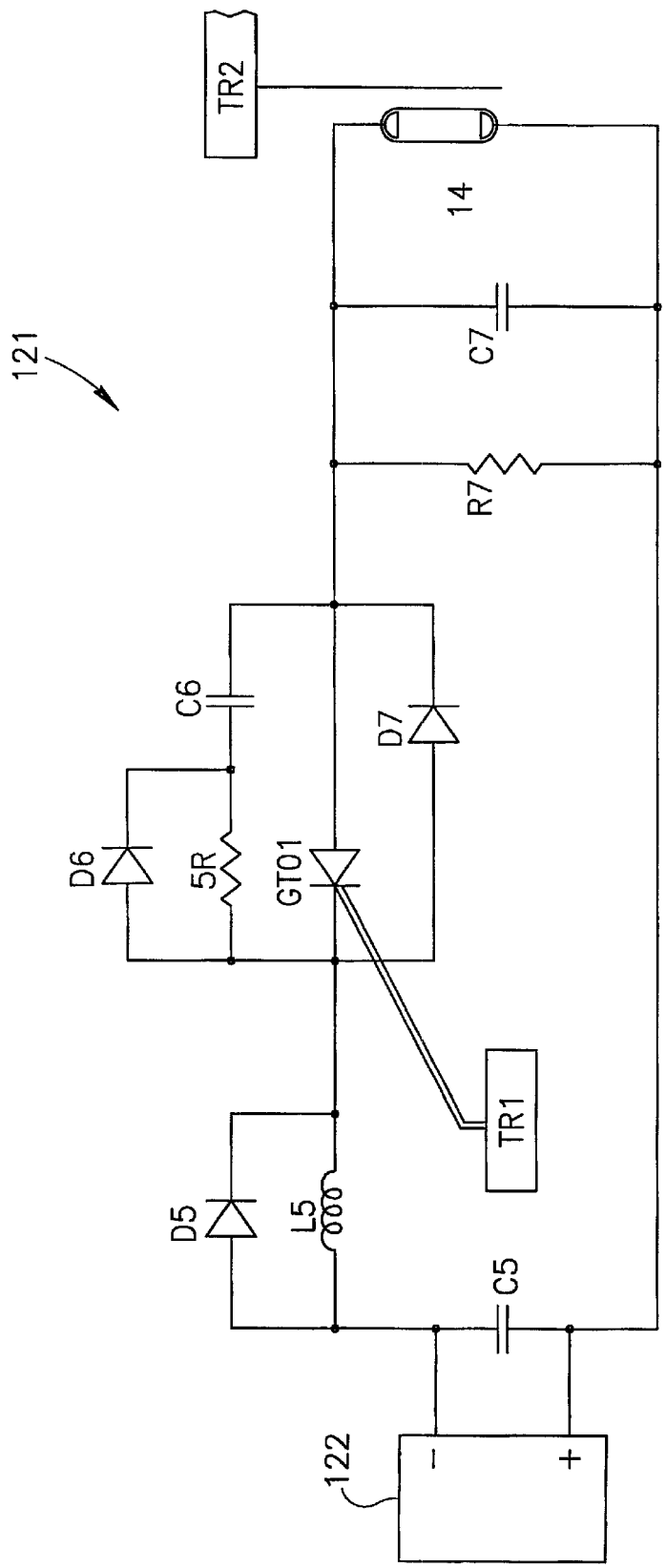
FIG. 19 shows a GTO driver circuit for a flashlamp.

In one alternative embodiment the pulse forming network of FIG. 3 is replaced by a GTO driver circuit 121, such as that shown in FIG. 19. The driver circuit of FIG. 19 uses a switch capable of being turned both on and off to control the application of power to the flashlamp. While this alternative embodiment will be described with respect to a GTO being used as the switch, other switches capable of being turned both on and off, such as IGBTs, may also be used.

Referring now to FIG. 19, driver circuit 121 includes a high voltage source 122, a capacitor bank C5, an inductor L5, a diode D5, a switch GTO1, a diode D6, a diode D7, a resistor R5, a capacitor C6, a GTO trigger generator TR1, a resistor R7, a capacitor C7 and a flashtube trigger generator TR2. These components are connected to flashlamp 14 and serve to provide the power pulses to flashlamp 14. The duration and timing of the pulses are provided in accordance with the description herein. Driver 121 operates in the manner described below.

High voltage source 122 is connected across capacitor bank C5, and charges capacitor bank C5 to a voltage suitable for application to flashlamp 14. Capacitor bank C5 may be a comprised of one or more capacitors, and may be configured in the manner described above.

Prior to illumination of flashlamp 14 flashtube trigger generator TR2 breaks down flashlamp 14 and creates a relatively low impedance channel therein. After the flashlamp breaks down, capacitor C7 dumps current into flashlamp 14, further creating a low impedance channel in flashlamp 14. In this manner a pre-discharge is provided that prepares flashlamp 14 for the power pulse. Capacitor C7 provides a small amount of current, relative to capacitor bank C5. Alternatively, driver circuit 121 may operate in a simmer mode, wherein the pre-discharge is not necessary.

Thereafter, switch GTO1 is turned on via a pulse from GTO trigger generator TR1, completing the circuit between flashlamp 14 and capacitor bank C5. Thus, capacitor bank C5 discharges through flashlamp 14. An inductor L5 may be provided to control the rise time of the current through flashlamp 14. Inductor L5 may include an inherent resistive component, not shown.

After a length of time determined by the desired pulse width has passed, GTO trigger generator TR1 provides a pulse to switch GTO1, turning it off. A control circuit determines the timing of the trigger pulses and provides them in accordance with the desired pulse widths and delays.

A snubber circuit comprised of diode D6, resistor R5, and a capacitor C6 is provided for switch GTO1. Also, didoes D5 and D7 are provided to protect switch GTO1 from reverse voltages. Resistor R7 is provided in parallel with flashlamp 14 to measure the leakage current of switch GTO1, which can in turn be used to make sure that switch GTO1 is operating properly.

A possible addition to driver circuit 121 is to provide an SCR or other switch in parallel with capacitor bank C5. This allows the discharge or resetting of capacitor bank C5 without turning on switch GTO1. Other modifications may be made, such as providing the circuit with a serial trigger, rather than the parallel trigger shown. Another modification is to use the driver circuit with a laser rather than flashlamp 14.

Proper use of pulse widths and delays can aid in avoiding burning the epidermis. The epidermis has a cooling time of about 5 msec, while large vessels have a longer cooling time (a 1 mm vessel has a cooling time of about 300 msec). Thus, during a pulse of duration longer than 5 msec the epidermis can cool down but the vessel will not. For example, for treatment of a large vessel (such as one having a diameter of about 1 mm a pulse of 100 msec will allow the skin to cool, but the vessel will not cool.

The same effect may be achieved using trains of pulses. This is useful when it is not practical to provide a single long pulse to the flashlamp. The delays between pulses are selected to allow the skin to cool, but to be too short for the vessel to cool. Thus, larger vessels can be treated with longer delays because they have greater cooling times. Small vessels cool quickly and long delays are not effective. However, they also need less energy and can be treated effectively in a single pulse. Typical delay times are in the range of 20 msec to 500 msec. More specifically, delays of between 100–500 msec are effective for vessels larger than 1 mm in diameter.

Delays of between 20–100 msec are effective for vessels between 0.5 and 1 mm in diameter. Delays of between 10–50 msec are effective for vessels between 0.1 and 0.5 mm in diameter. A single pulse having a width in the range of 1 msec to 20 msec is effective for vessels less than 0.1 mm diameter.

Additionally, delays should be selected according to skin pigmentation. Darker skin absorbs more energy and needs more time to cool: thus longer delays are needed. Lighter skin absorbs less energy and can accommodate shorter delays.

It has been found that multiple pulses avoids "purpora" or the explosion of small vessels in or close to the skin. The use of pulses to avoid burning and provide cooling will be effective for light provided by lasers or other sources as well.

Another alternative embodiment includes the use of a microprocessor or personal computer to control the flashlamp. The microprocessor can be used to provide the timing functions and prompt the trigger signals described above. Additionally, in one embodiment the microprocessor includes a user interface, such as a screen and keyboard, buttons, mouse, or other input device. The microprocessors have information stored therein that aids in the selection of treatment parameters.

For example, if the condition being treated is a port wine stains skin type III, the physician inputs that condition into the microprocessor. The microprocessor responds with suggested treatment parameters, such as using a 570 nm cut-off filter, a double pulse with a delay of 50 msec and a fluence of 55 J/cm$^2$. The physician can alter these suggested parameters, but need not refer back to operating guidelines for suggested parameters. This alternative may be used with light sources other than a flashlamp, such as UV or a pulsed laser.

These output parameters are shown on a display such as a screen or printer, and include the outputs discussed below. This will aid the physician in determining the proper treatment and in learning how to effectively use such devices. In one embodiment the microprocessor output on the display shows a simulation of interaction of light with skin and vascular lesions, oxygen concentration and temperature distribution in malignant tissue being illuminated for the purpose of cancer by a flashlamp, or processes occurring in skin resurfacing using infrared lasers or other sources.

A program within the microprocessor (or alternatively an analog circuit) models interaction of light with tissue and vessels. Many programs may be used to carry out the modeling, and in the preferred embodiment the following input parameters are used: light source type (flashlamp or pulsed laser e.g.); number of output curves (1–4 e.g.); skin type; vessel diameter and depth; blood type (oxy or deoxyhemoglobin); pulse duration; delay between pulses; energy fluence; type of filter; short or long pulse mode; is a gel being used and its temperature. For a pulsed laser the wavelength is an input (400–1064 nm e.g.).

The microprocessor and the screen show the following information in one embodiment: temperature distribution in the tissue and in the vessel at the end of treatment; graphs of up to four curves to compare different light sources or treatment regime. Alternatively, the outputs could be printed rather than shown on a screen.

One skilled in the art will recognize that many microprocessor routines may be used to implement the invention. The routines may model the interactions in many ways, and one such model for single dimensional light interaction with a tissue uses the following empirical expression for fluence:

$$F = F(0) \exp(-x/d)$$

where $d = 1/\mu_{eff}$ and $\mu_{eff} = [3\mu_s(\mu_s + \mu_s(1-g))]^{1/2}$

Where $\mu_s$ is an absorption coefficient of dermis, $\mu_s$, is a scattering coefficient of dermis, and g is the anisotropy factor which is defined as average cosine of scattering angle for one scattering event.

F(0) was calculated in accordance with *Diffusion of Light in Turbid Material*, A. Ishimaru, Applied Optics, 1989 Vol. 28 No. 12, pp 2210–2215, but an empirical correction depending on wavelength is added:

$$F(0) = Fo(640/W)^{1/4}$$

where W is a wavelength.

Light relaxation time in the tissue is significantly less than the temperature relaxation time and light pulse durations used for treatment of skin lesions, therefore a stationary model for description of light penetration into the tissue was used. Ishimaru's hydrodynamic model is suitable for calculating of F(0). Accordingly to this model, the diffuse energy fluence rate $\psi_d$ satisfies the following diffusion equation:

$$(\nabla^2 - K^2)\psi_a = -Q$$

$$Q = 3\gamma_s(\gamma_\tau + g\gamma_a)F_o \exp(-\tau)$$

$$k^2 = 3\gamma_s\gamma_a$$

$$\gamma_{tr} = \gamma_s(1-g) + \gamma_a$$

$$\gamma_t = \gamma_a + \gamma_s$$

$$\tau = \int \gamma_t ds$$

where Fo is the incident energy beam. Scattering and absorption coefficients are functions of wavelength. The total energy fluence rate is given by $$\psi_t = \psi_a + \psi_c$$

$$\psi_c = F_o \exp(-\tau)$$

This equation was calculated numerically with the corresponding boundary conditions. The boundary condition for $\psi_d$ at the surface illuminated by the incident intensity is $$\psi_d + 2/3\gamma_{tr}\cdot\psi_d + 2\gamma_s gF_a/\gamma_{tx} = 0$$

Temperature distribution behavior in the tissue is described by solution of the 1-D heat conductivity equation in planar geometry for near epidermis area $$\rho c \cdot \partial T/\partial T = \lambda \partial^2 T/\partial x^2 + \gamma_a \psi_t$$

with initial and boundary conditions $$T_{T=0} = 36$$

$$\partial T/\partial x_{x=0} = 0$$

Here ρ is the density of tissue, c is the specific heat and λ is the heat conductivity coefficient. The thermal properties of water were assumed for the thermal properties of tissue.

A heat conductivity equation is calculated in cylindrical geometry for near vessel area, where the center of the cylinder was chosen as point with maximal temperature.

$$\rho c \partial T/\partial \gamma = \lambda \partial^2 T/\partial x^2 + 1/r\, \partial T/\partial x + \gamma_a \psi_t$$

As one skilled in the art should recognize other models may be used as well.

The microprocessor or personal computer can also be used to create and store patient information in a database. Thus, past treatment information such as condition being treated, treatment parameters, number of treatments, etc. is stored and may be recalled when the patient is again treated. This aids in providing the proper treatment to the patient. Additionally, the database may include photographs of the patient's condition before and after each treatment. Again, this aids in record keeping and determining what treatments are most successful for given conditions.

In addition to the treatments described above the devices and methods described herein may be used to treat other conditions. For example, psoriasis and warts have been successfully treated. Similarly, skin rejuvenation (treating wrinkles) should be effective. The inventor further contemplates using this invention to treat hemorrhoids, throat lesions, and gynecological problems associated with vascular malformations. In addition, hair depilation can also be effected.

In the use of hair depilation in accordance with the present invention, hair is removed by exposing the "hairy" area to intense, wide area, pulsed electromagnetic (light) energy. The energy heats the hair and coagulates the tissue around the hair and follicle without damaging the healthy skin.

An optically transparent water based gel may be applied to the skin prior to treatment. As used herein gel means a viscous fluid that is preferably, but not necessarily water based. The gel is used to cool the epidermis which is the primary location of light absorption by tissue, due to the melanin content of the epidermis. The gel is applied so as not to penetrate into the cavity generated by the hair follicle, and thus does not cool the hair and the hair follicle. As a result the energy is selectively applied to coagulate the hair without damaging the skin.

It is desirable that a spatially dispersed field of light be used for treatment of the skin, in accordance with the invention. By spatially dispersed, it is intended that the field of light be spread over an extended area, as would be apparent from the term to one of ordinary skill in the art. Accordingly, any apparatus or combination of elements suitable for producing a dispersed field of light on the skin, as opposed to a narrow beam of light on the skin, can be used.

A polychromatic light source, such as a high intensity pulsed flashlamp, is an example of a source suitable for the purposes described herein. One advantage of a polychromatic source such as a flashlamp is that energy having a wavelength in the range of 550 to 630 nm is heavily absorbed in blood and can be used to coagulate the vessel that feeds the hair. Additionally, longer wavelengths, in the range of 600 to 1100 nm have a very good penetration into non-pigmented skin. This wavelength range can be used to couple to the melanin of the hair. The higher pigmentation of the hair and the hair follicle can enhance the absorption of energy by the hair.

Flashlamps also have the advantage of being able to illuminate a large area, thus minimizing the treatment time. The flashlamp combined with a proper reflector can deliver the required fluences to areas on the order of a few square centimeters in a single application. However, other light sources, such as pulsed lasers can be used as well.

Figure 20:
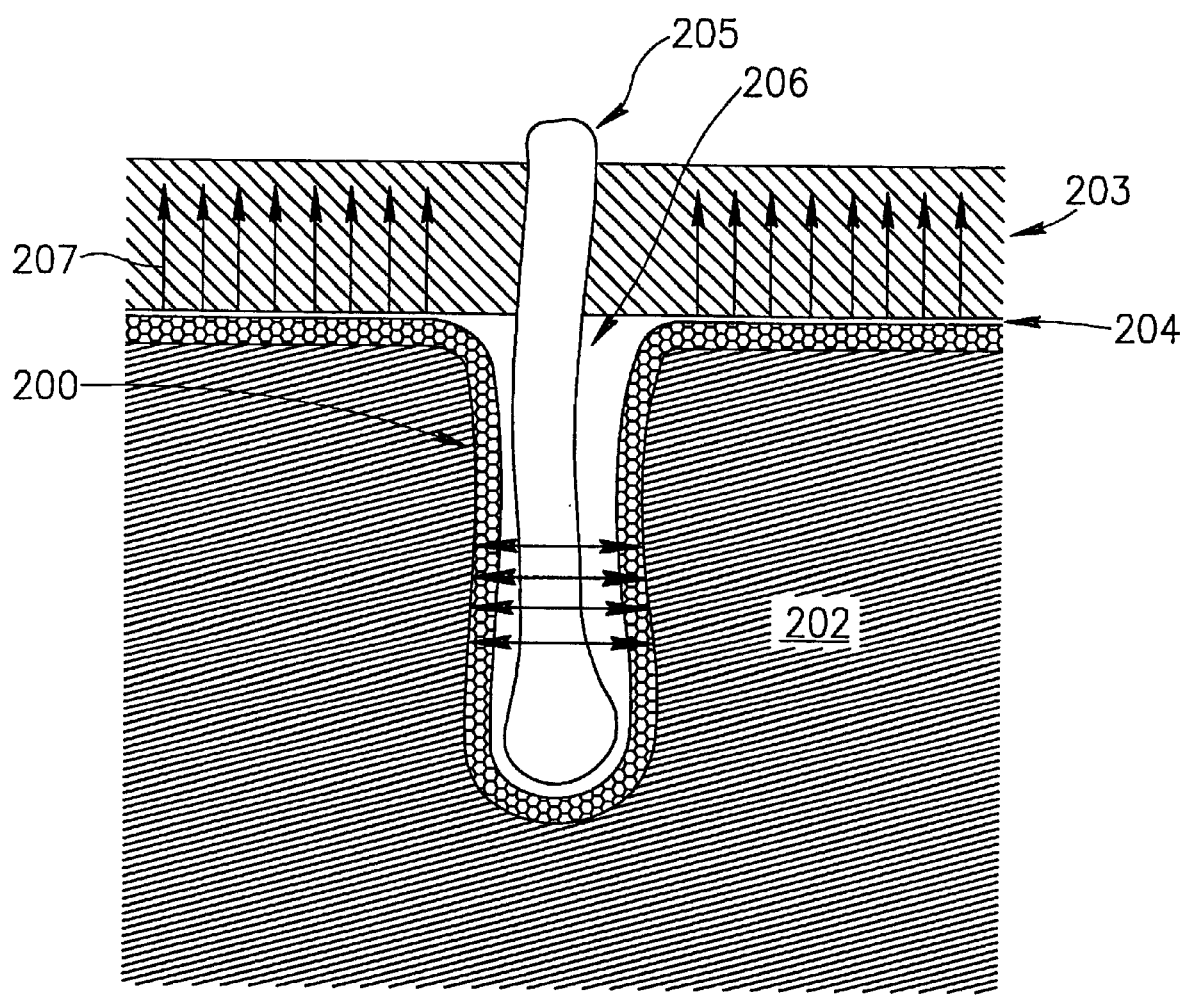
FIG. 20 is a schematic drawing of a cross section of a hair follicle in the dermis and a gel applied to the epidermis in accordance with the present invention.

Referring now to FIG. 20, a schematic drawing of a cross section of a hair follicle 200 in a dermis 202 is shown. As may be seen in FIG. 20, a gel 203 applied to an epidermis 204. In the present invention, water based transparent gel 203 is applied to a large section of the skin that is covered by hair, such as hair 205. Gel 205 is applied to epidermis 204 and creates a thin layer on top of epidermis 204. This layer is closely coupled to epidermis 204 and acts as a heat sink that cools epidermis 204 when light (electromagnetic energy) is applied to the area. As may also be seen in FIG. 20, gel 203 does not penetrate into a cavity 206 formed by hair follicle 200 due to its surface tension properties and the fact that the hair is naturally covered by a thin layer of fatty material which makes it hydrophobic. The much higher heat diffusivity of gel 203 compared to that of air which fills cavity 206 enables fast cooling of epidermis 204, represented by arrows 207, while hair 205 is cooled at a much slower rate.

The cooling time—$\delta t$ of an object that has typical dimensions d and diffusivity—$\alpha$ can be written as:

$$\delta t = d^2/16\alpha$$

The epidermis has typical cross dimensions of less than 0.1 mm, which is also the typical diameter of hair. The diffusivity of water is approximately $\alpha = 3 \times 10^{-9} m^2 sec^{-1}$.

The gel is applied, in the manner shown in FIG. 20, over a wide area. When the gel is so applied the typical cooling time of the hair will be on the order of 200 msec and that of the epidermis will be on the order of 5 msec. This difference in cooling times is due to the fact that the gel does not penetrate into the hair follicles. It is preferable to use a transparent gel since the gel acts only as a cooling agent and should not be heated by the external illumination.

In accordance with the invention, light is applied to the treated area in either a long pulse or in a sequence of pulses separated by a delay. The delay and/or pulse length is preferably controlled by the operator to provide enough heat to remove the hair but not enough heat to damage the skin. For example, the pulse length or delay between the pulses should be more than the cooling time of the gel covered epidermis and less than the cooling time of the hair and follicle. Thus, referring to the above discussion on cooling times, a pulse length of 50 msec if a single pulse is used or a delay of 50 msec between the pulses if a pulse sequence is used are appropriate values. The spectrum of the light source may be selected with reference to the absorption by the skin, by the hair and by the blood vessels feeding the hair. For example, the hair follicle has typical a depth of 1 to 2 mm. It is preferable, therefore, to use a light wavelength range that can penetrate into this depth without very high attenuation.

Figure 21:
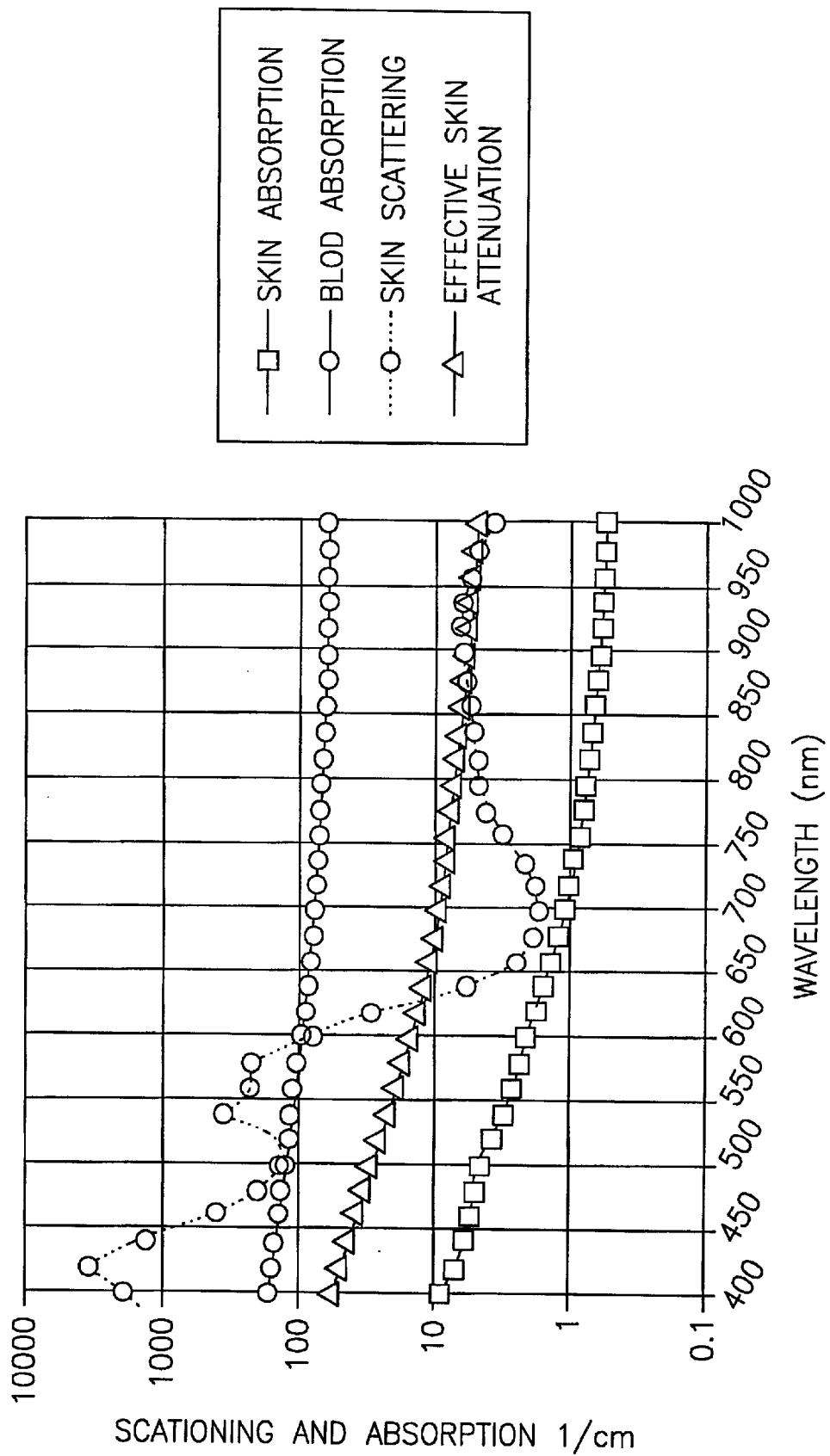
FIG. 21 is a graph showing the optical properties of the skin.

FIG. 21 is a graph showing the scattering, absorption and effective attenuation coefficients in fair skin dermis and the absorption coefficient of blood in the 400 to 1000 nm range. Because a wide area is illuminated, rather than a single hair, it is preferable to use a wavelength range that penetrates into the skin without being highly attenuated. The skin attenuation coefficient controls the depth of penetration of light into the skin. As may be seen in FIG. 21 wavelengths that are longer than 550 nm will be more effective to penetrate deep enough into the skin. Shorter wavelengths are less desirable because they will be highly attenuated before reaching the lower parts of the hair follicles.

Wavelengths significantly longer than 1,000 nm are also less effective due to high absorption of infrared in water which constitutes more than 70% of skin. Wide area photo thermal hair removal of the present invention preferably uses light that can penetrate deep into the skin, since light is coupled to the hair and the hair follicles only after it penetrates through the skin. Most of the spectrum of light at wavelengths longer than 1,300 nm is heavily absorbed in water and will be less useful because it does not penetrate very deep into the skin. For example, $CO_2$ laser radiation in the 10,000 nm range penetrates only a few tens of microns into the skin.

Figure 22:
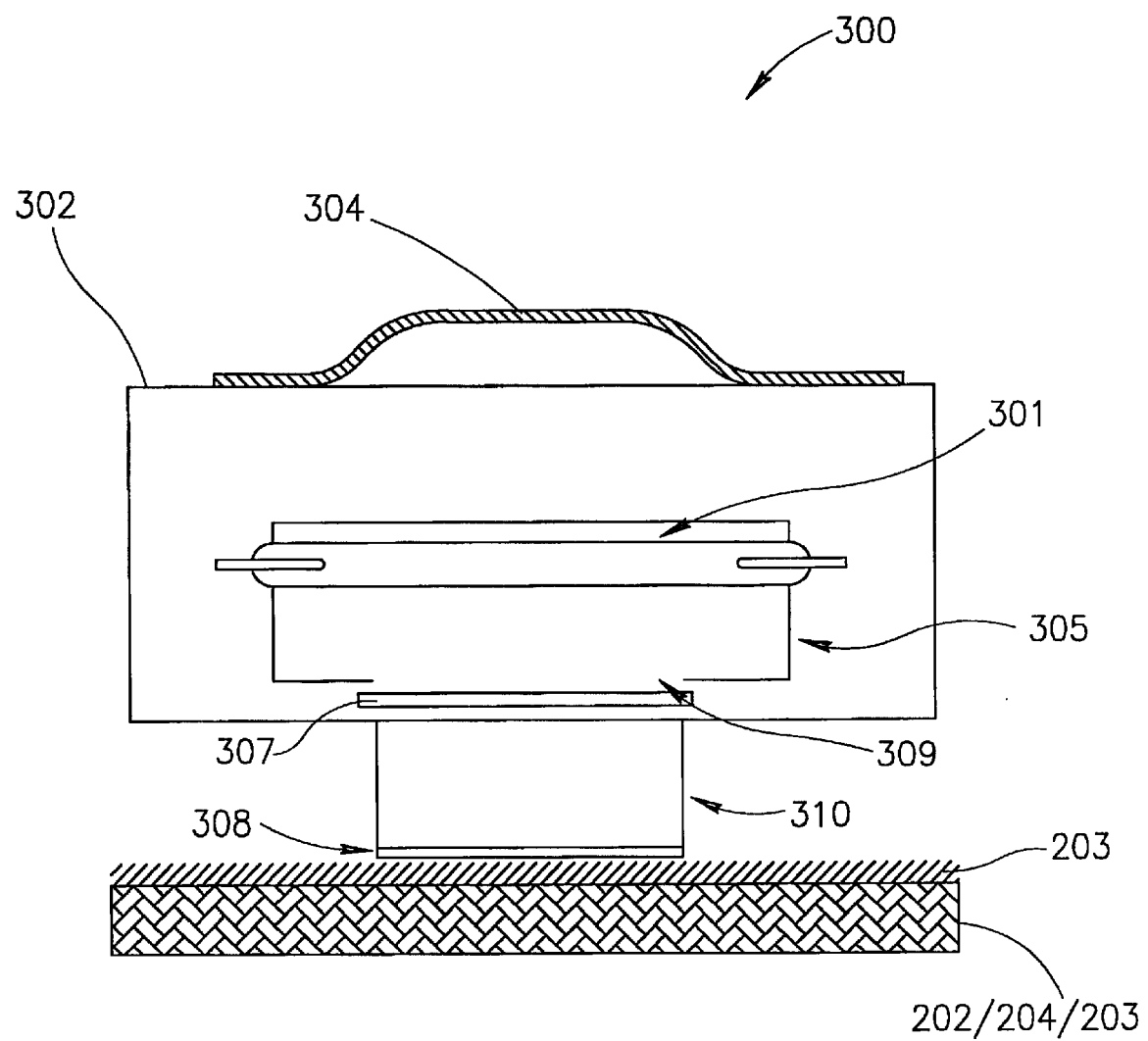
FIG. 22 is a side view of a hair removal apparatus constructed in accordance with the present invention.
Figure 23:
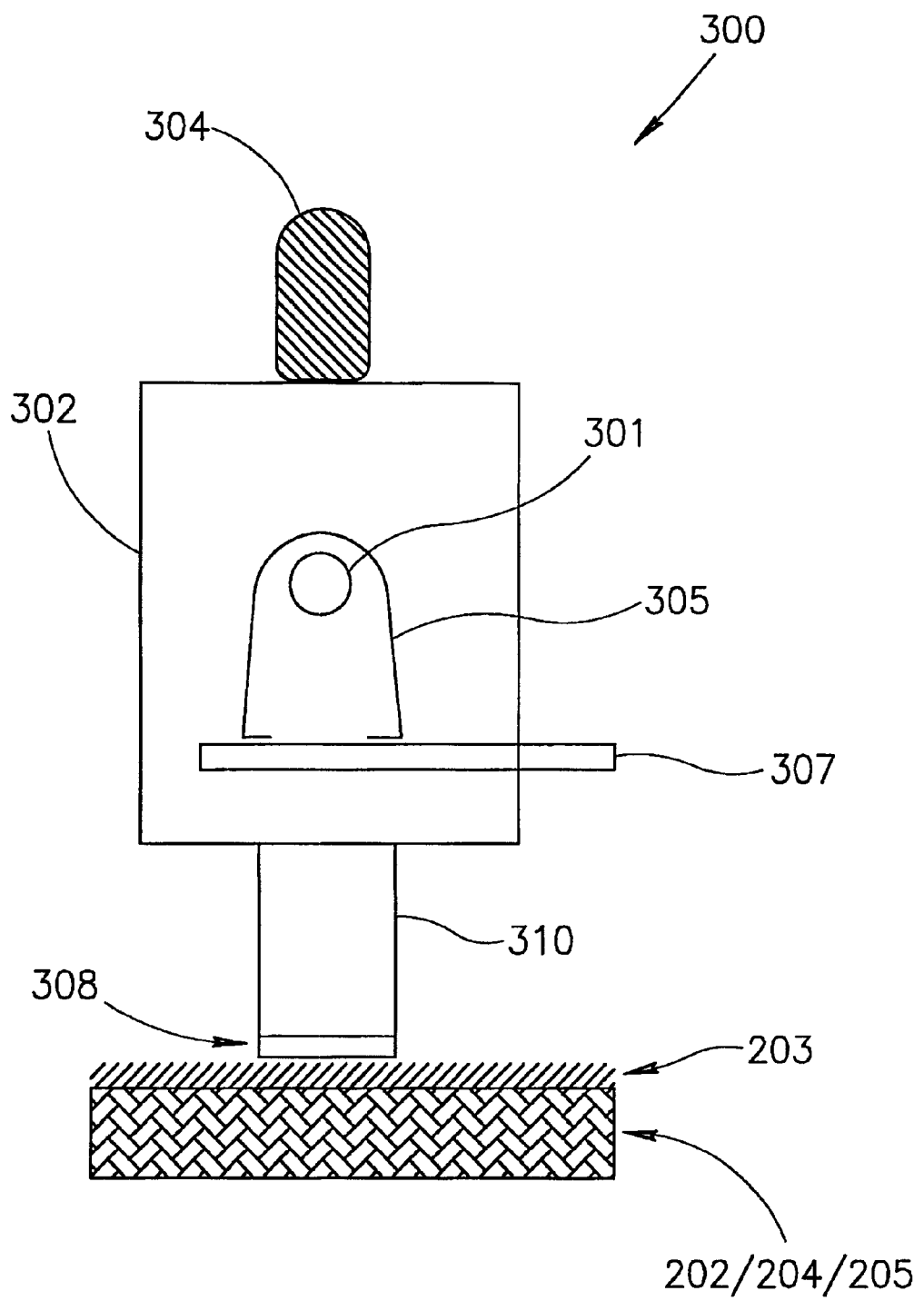
FIG. 23 is a front view of a hair removal apparatus constructed in accordance with the present invention.

Referring now to FIGS. 22 and 23, one preferred embodiment of hair remover 300 includes a flashlamp 301 located in a housing 302 having a handle. The flashlamp is shown adjacent gel 203 and hairy skin 202/204/205. One flashlamp that the inventors have found effective for hair removal is described in detail in co-pending U.S. patent application For Method and Apparatus For Therapeutic Electromagnetic Treatment, Ser. No. 07/964,210, filed Oct. 20, 1992 and issued as U.S. Pat. No. 5,405,368, and incorporated herein by reference. The flashlamp described therein provides a suitable fluence and it illuminates a large area in a single pulse (on the order of 10×50 mm).

Such a flashlamp is driven by a variable pulse width power source. The flashlamp is contained in housing 302 and the light from the flashlamp is directed towards the skin by a reflector 305 that has a high reflectivity.

Also shown in FIGS. 22 and 23 is a filter 307, that is disposed between flashlamp 301 and gel 203. The filter, or in an alternative embodiment, multiple filters, are used to control the spectrum generated by the light source. As used herein filter, or band-pass filter, describes a device that allows electromagnetic energy (light) of certain wavelengths or frequencies to pass. The other wavelengths or frequencies are either partially or wholly removed.

The operator can select the filter according to the skin pigmentation of the person being treated. For the embodiment using a flashlamp, one can take advantage of the spectral range typically generated by such a lamp, which is in the range of 200 to 1300 nm for high pressure xenon flashlamps operated at high current densities (on the order of 1,000 to 5,000 $A/cm^2$). Since hair removal is mainly done for cosmetic reasons and is mostly important for cases of darker hair, the hair itself will absorb light in a wide spectral range in the visible and the near infrared. The shorter wavelengths generated by the flashlamp may be removed since they do not penetrate as deeply into the skin (as can be seen from FIG. 21).

In one embodiment a long pass filter that transmits only wavelengths longer than the cut off wavelength of the filter is used. A cut off wavelength of 600 nm is used in a preferred embodiment when the person being treated has fair skin. A cut off wavelength in the range of 700 to 800 nm is used in the preferred embodiment to treat people with dark skin. According to the invention, the filters may be, for example, dichroic filters or absorbing filters. The desired spectrum can also be achieved by more than one filter or by band-pass filters.

Light from flashlamp 301 is coupled to the skin through a transparent window 308 and a coupler 310 (described below). As shown in FIGS. 22 and 23, window 308 is placed on transparent water based gel 203. In use, the operator holds hair remover 300 by handle 304, and places it on the area of skin where treatment is desired (and gel 203 has been applied). Transparent window 308 creates a well defined flat surface on gel 203, through which light enters into gel 203 and into the skin.

The operator selects the pulse and energy fluence parameters on a control unit (not shown). The power and control unit are preferably housed in a separate box and will include power from a capacitor charged to a high voltage by a DC power supply, wherein the capacitor is discharged through the flashlamp. Hair remover 300 can be connected to the power and control unit via a flexible cable that allows easy aiming of the device when aiming it to the treatment area on the patient's skin. Pulse length control can be achieved by using a few pulse forming networks that can generate different pulse widths. Alternatively, an opening 309 may include a solid state opening switch that can stop the discharge at a time preset by the operator, thus controlling the pulse width. These elements of the device are well known and can be easily constructed, or replaced by similar elements, as one skilled in the art will know.

After the parameters have been selected, the operator fires the unit by pressing a switch that can be located in a variety of locations. A total fluence on the order of 10 to 100 $J/cm^2$ will successfully remove the hair. This fluence can be determined from the requirement of reaching a high enough temperature of the hair and hair follicle, and considering the penetration of light, through the skin and into the hair and hair follicle, absorption of light in the hair and hair follicle, specific heat capacity of the hair and the hair follicle, and the cooling of the hair during the pulse by heat conductivity to the surrounding skin.

Coupler 310 transmits light from flashlamp 301 to gel 203 and to the skin. The coupler can be comprised of a hollow box with internally reflecting walls that act as a light guide for the light generated by flashlamp 301, to transmit the light (electromagnetic energy) to the skin. Coupler 310 may alternatively be made from other material, for example, a solid transparent material such as glass or acrylic in which light reflection from the walls is achieved by using total internal reflection on the side walls.

Coupler 310 is used, in one alternative embodiment, to control the angular distribution of the light rays impinging on the skin. Light rays will hit the hair or the hair follicle predominantly when they are travelling in a direction perpendicular to the plane of the skin. A distribution of light rays that has a relatively wide angular divergence when treating shallow hair is desirable to direct a large portion of the energy to the hairs and follicles. Conversely, a narrow divergence is preferable when deep penetration is desired.

In one embodiment both shallow and deep penetration is obtained by a using a two stage treatment process. A narrow divergence beam is used first to treat the deeper hair follicles, while a high divergence beam is used to treat the top of the hair follicles.

Figure 24:
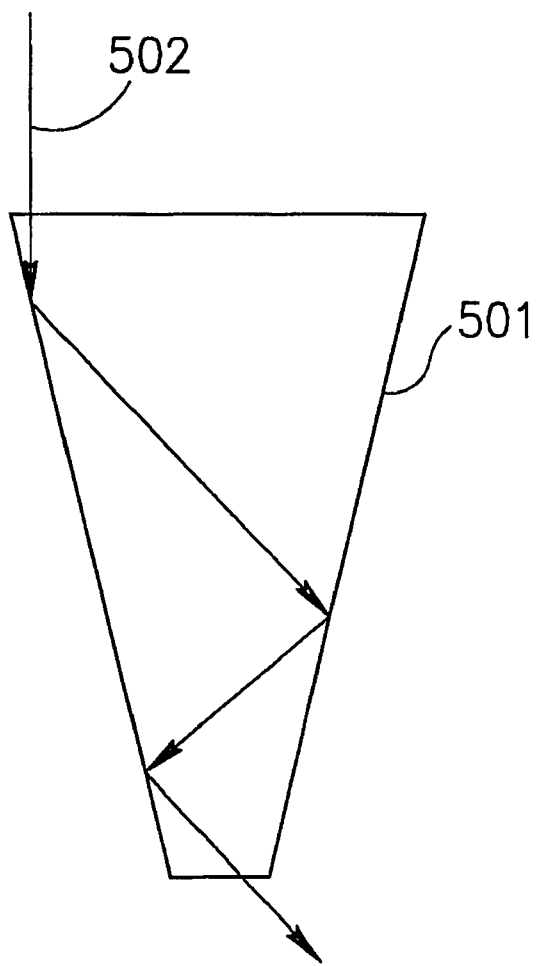
FIG. 24 is a divergent coupler such as one used in the present invention.

FIG. 24 shows a coupler 501 having an exit beam with a greater angular divergence than that of the entrance beam. As shown in FIG. 24, a beam 502 enters coupler 501 at a small angle, relative to the axis of coupler 501. When beam 502 exits coupler 501 the angle, relative to the axis, is much greater. The tapered shape of coupler 501 enhances this divergence.

Figure 25:
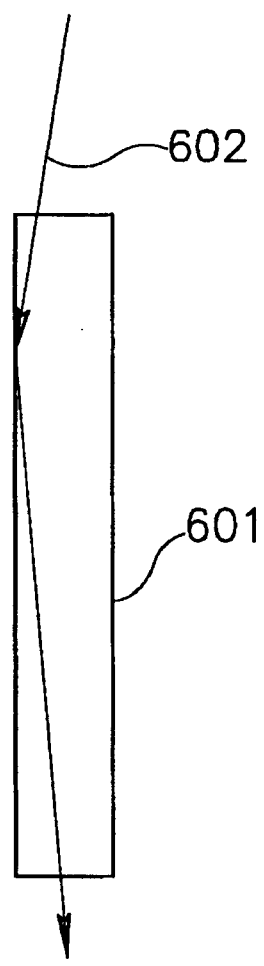
FIG. 25 is a non divergent coupler such as one used in the present invention.

FIG. 25 shows a straight coupler 601, that maintains the angular distribution of the rays of light that enter into it. A beam 602 is shown entering and exiting coupler 601 with the same angle, relative to the axis of coupler 601. Alternate use of both couplers 501 and 601 can achieve the narrow and deep penetration discussed above. Alternatively, the user can select the type of coupler according to the depth of hair being treated.

Clinical tests have been performed on hair on the legs of a few patients. Hair was removed for at least two months without observing any hair growing back on the exposed areas during this period. The experiments were performed with high fluences, i.e., up to 45 J/cm$^2$ in each exposure. The spectrum used covered the range of 570 to 1100 nm and the fluence was supplied in a triple pulse with delays of 50 to 100 msec between pulses. The pulse sequence enabled hair removal with minimum pain and no damage to the skin. The transparent gel that was used in these experiments was a water based ultrasound gel, such as that commonly available.

Thus, it should be apparent that there has been provided in accordance with the present invention various inventions that fully satisfy the objectives and advantages set forth above. Although the inventions have been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method for applying electromagnetic radiation to the skin, the method comprising:

generating electromagnetic radiation having a plurality of wavelengths ranging over the visible section of the electromagnetic spectrum and over at least parts of the ultra-violet and infra-red sections of the electromagnetic spectrum;

filtering a substantial part of said plurality of wavelengths in the ultra-violet section of the electromagnetic spectrum, thereby producing filtered electromagnetic radiation ranging over a substantial part of the visible and at least part of the infra-red sections of said generated electromagnetic radiation; and applying said filtered electromagnetic radiation to the skin.

2. A method according to claim 1 comprising applying a gel to the skin.

* * * * *

(12) EX PARTE REEXAMINATION CERTIFICATE (7134th)
United States Patent
Eckhouse et al.

(10) Number: US 6,514,243 C1
(45) Certificate Issued: *Nov. 3, 2009

(54) METHOD AND APPARATUS FOR ELECTROMAGNETIC TREATMENT OF THE SKIN, INCLUDING HAIR DEPILATION

(75) Inventors: Shimon Eckhouse, Haifa (IL); Hillel Bachrach, Needham, MA (US)

(73) Assignee: Lumenis Ltd., Yokneam (IL)

Reexamination Request:
No. 90/010,265, Sep. 2, 2008

Reexamination Certificate for:
Patent No.: 6,514,243
Issued: Feb. 4, 2003
Appl. No.: 09/505,998
Filed: Feb. 17, 2000

( * ) Notice: This patent is subject to a terminal disclaimer.

Related U.S. Application Data

(63) Continuation of application No. 08/912,764, filed on Aug. 18, 1997, now Pat. No. 6,280,438, which is a continuation-in-part of application No. 08/508,129, filed on Jul. 27, 1995, now Pat. No. 5,720,772, which is a continuation-in-part of application No. 08/477,479, filed on Jun. 7, 1995, now Pat. No. 5,620,478, which is a continuation of application No. 08/473,532, filed on Jun. 7, 1995, now Pat. No. 5,755,751, which is a continuation of application No. 08/383,509, filed on Feb. 3, 1995, now Pat. No. 5,626,631, which is a continuation-in-part of application No. 07/964,210, filed on Oct. 20, 1992, now Pat. No. 5,405,368, which is a continuation-in-part of application No. 08/412,519, filed on Mar. 29, 1995, now Pat. No. 5,683,380.

(51) Int. Cl.
*A61B 18/18* (2006.01)

(52) U.S. Cl. .................. 606/9; 606/3; 606/10; 607/88
(58) Field of Classification Search .................. None
See application file for complete search history.

(56) References Cited

U.S. PATENT DOCUMENTS

| | | | |
|---|---|---|---|
| 2,716,698 A | 8/1955 | Brukner | 240/1 |
| 2,954,771 A | 10/1960 | Boyan | 128/396 |
| 3,327,712 A | 6/1967 | Kaufman et al. | 128/398 |
| 3,693,623 A | 9/1972 | Harte et al. | 128/303.1 |
| 3,834,391 A | 9/1974 | Block | 128/303.1 |
| 3,930,504 A | 1/1976 | de Laforcade | 128/303.1 |
| 4,112,335 A | 9/1978 | Gonser | 315/241 R |
| 4,229,658 A | 10/1980 | Gonser | 250/504 H |
| 4,232,678 A | 11/1980 | Skovajsa | 128/395 |
| 4,233,493 A | 11/1980 | Nath | 219/354 |
| 4,283,661 A | 8/1981 | Doty | 315/360 |
| 4,298,005 A | 11/1981 | Mutzhas | 128/396 |
| 4,321,930 A | 3/1982 | Jobsis et al. | 128/633 |
| 4,366,570 A | 12/1982 | Bees | 372/70 |
| 4,380,240 A | 4/1983 | Jobsis et al. | 128/633 |
| 4,388,924 A | 6/1983 | Weissman et al. | 128/303.1 |
| 4,444,190 A | 4/1984 | Mutzhas | 128/396 |
| 4,497,018 A | 1/1985 | Rice | 363/96 |
| 4,506,196 A | 3/1985 | Bees | 315/241 R |
| 4,539,987 A | 9/1985 | Nath et al. | 128/303.1 |
| 4,560,883 A | 12/1985 | Kerschgens | 250/504 |
| 4,564,011 A | 1/1986 | Goldman | 128/303.1 |
| 4,645,980 A | 2/1987 | Yang | 315/159 |

(Continued)

FOREIGN PATENT DOCUMENTS

| DE | 27 17 421 A1 | 11/1978 |
|---|---|---|
| JP | H3-128069 | 5/1991 |
| JP | HEI4-53569 | 2/1992 |

(Continued)

OTHER PUBLICATIONS

Gros, et al, Diaphanologie Mammaire, Memoires Originaux, J. Radiol. Electrol, pp. 297–306, vol. 53, No. 4, 1972.

(Continued)

*Primary Examiner*—Beverly M. Flanagan

(57) ABSTRACT

Apparatus and methods for electromagnetic skin treatment, including the removal of hair. Devices include pulsed light sources such as flashlamps for providing electromagnetic treatment of the skin, including hair removal. The devices and methods provide for the removal of large numbers of hairs at the same time, rather than on a hair by hair basis.

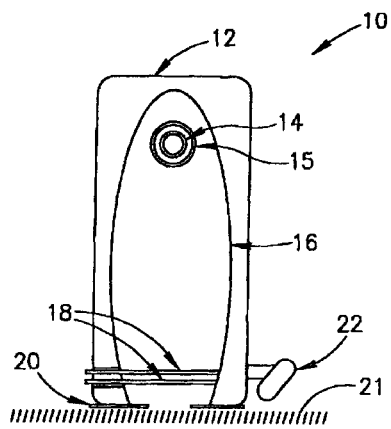

U.S. PATENT DOCUMENTS

| | | | |
|---|---|---|---|
| 4,647,830 A | 3/1987 | Bees | 320/1 |
| 4,653,495 A | 3/1987 | Nanaumi | 128/303.1 |
| 4,672,969 A | 6/1987 | Dew | 128/397 |
| 4,726,377 A | 2/1988 | Jegers et al. | 128/376 |
| 4,729,375 A | 3/1988 | Jegers et al. | 128/375 |
| 4,733,660 A | 3/1988 | Itzkan | 128/303.1 |
| 4,775,361 A | 10/1988 | Jacques et al. | 604/20 |
| 4,810,658 A | 3/1989 | Shanks et al. | 436/172 |
| 4,829,262 A | 5/1989 | Forumoto | 330/4.3 |
| 4,835,749 A | 5/1989 | Welton | 368/10 |
| 4,839,562 A | 6/1989 | Francis et al. | 315/149 |
| 4,851,738 A | 7/1989 | Yang | 315/159 |
| 4,871,559 A | 10/1989 | Dunn et al. | 426/248 |
| 4,884,568 A | 12/1989 | Hahn | 128/303.1 |
| 4,930,504 A | 6/1990 | Diamantopoulos et al. | 128/395 |
| 4,938,262 A | 7/1990 | Tuffel | 128/401 |
| 4,947,859 A | 8/1990 | Brewer et al. | 128/715 |
| 5,008,579 A | 4/1991 | Conley et al. | 310/303 |
| 5,020,995 A | 6/1991 | Levy | 433/215 |
| 5,034,235 A | 7/1991 | Dunn et al. | 426/238 |
| 5,039,867 A | 8/1991 | Nishihara et al. | 250/492.3 |
| 5,054,488 A | 10/1991 | Muz | 128/633 |
| 5,059,192 A | 10/1991 | Zaias | 606/9 |
| 5,066,293 A | 11/1991 | Furumoto | 606/9 |
| 5,071,422 A | 12/1991 | Watson et al. | 606/128 |
| 5,083,093 A | 1/1992 | Adler et al. | 328/65 |
| 5,113,462 A | 5/1992 | Clancy et al. | 385/53 |
| 5,125,922 A | 6/1992 | Dwyer et al. | 606/3 |
| 5,126,621 A | 6/1992 | Morton et al. | 313/237 |
| 5,194,723 A | 3/1993 | Cates et al. | 250/205 |
| 5,204,517 A | 4/1993 | Cates et al. | 250/205 |
| 5,226,107 A | 7/1993 | Stern et al. | 392/416 |
| 5,269,778 A | 12/1993 | Rink et al. | 606/12 |
| 5,281,798 A | 1/1994 | Hamm et al. | 250/205 |
| 5,282,797 A | 2/1994 | Chess | 606/9 |
| 5,290,273 A | 3/1994 | Tan | 606/9 |
| 5,290,274 A | 3/1994 | Levy et al. | 606/13 |
| 5,312,395 A | 5/1994 | Tan et al. | 606/9 |
| 5,320,618 A | 6/1994 | Gustafsson | 606/9 |
| 5,328,488 A | 7/1994 | Daikuzono | 606/16 |
| 5,328,517 A | 7/1994 | Cates et al. | 134/7 |
| 5,334,190 A | 8/1994 | Seiler | 606/5 |
| 5,337,741 A | 8/1994 | Diamond | 600/8 |
| 5,344,418 A | 9/1994 | Ghaffari | 606/9 |
| 5,344,433 A | 9/1994 | Talmore | 607/88 |
| 5,374,265 A | 12/1994 | Sand | 606/5 |
| 5,400,791 A | 3/1995 | Schlier et al. | 128/664 |
| 5,423,803 A | 6/1995 | Tankovich et al. | 606/9 |
| 5,445,146 A | 8/1995 | Bellinger | 607/89 |
| D363,349 S | 10/1995 | Dittert | D24/158 |
| 5,474,528 A | 12/1995 | Meserol | 604/20 |
| 5,489,279 A | 2/1996 | Meserol | 604/290 |
| 5,522,814 A | 6/1996 | Bernaz | 606/36 |
| 5,546,214 A | 8/1996 | Black et al. | 359/203 |
| 5,558,666 A | 9/1996 | Dewey et al. | 606/9 |
| 5,595,568 A | 1/1997 | Anderson et al. | 606/9 |
| 5,618,284 A | 4/1997 | Sand | 606/5 |
| 5,658,323 A | 8/1997 | Miller | 607/89 |
| 5,725,565 A | 3/1998 | Smith | 607/88 |
| 5,755,753 A | 5/1998 | Knowlton | 607/98 |
| 5,814,040 A | 9/1998 | Nelson et al. | 606/9 |
| 5,817,089 A | 10/1998 | Tankovich et al. | 606/9 |
| 5,817,090 A | 10/1998 | Abergel et al. | 606/9 |
| 5,843,143 A | 12/1998 | Whitehurst | 607/88 |
| RE36,634 E | 3/2000 | Ghaffari | 606/9 |
| 6,171,332 B1 | 1/2001 | Whitehurst | 607/89 |

FOREIGN PATENT DOCUMENTS

| | | |
|---|---|---|
| JP | 4-90360 | 8/1992 |
| SE | 465 953 B | 11/1991 |
| WO | WO 89/00871 | 2/1989 |
| WO | WO 90/14836 | 12/1990 |
| WO | WO 91/15264 | 10/1991 |
| WO | WO98/52645 | 11/1998 |

OTHER PUBLICATIONS

Gros, et al, Diaphanologie Mammaire, Memoires Originaux, *J. Radiol. Electrol.,* 53(4):297–306 (1972), in French, with English translation.

Brochure for an Infrared Coagulator by Redfield Corporation (1968).

Groot & Johnson, "Laser and Advances Dermatological Instrumentation", *Australas J. Dermatol.,* 28:77–85 (1987).

Kaufmann et al., "Pulsed Er:YAG– and 308 nm UV–Excimer Laser: An In Vitro and In Vivo Study of Skin–Ablative Effects", *Laser Surg. Med.,* 9:132–140 (1989).

Achauer et al., "Argon Laser Treatment of Telangiectasia of the Face and Neck: 5 Year' Experience", *Lasers Surg. Med.,* 7:495–498 (1987).

Alora et al., "Recent Developments in Cutaneous Lasers", *Lasers Surg. Med.,* 26:108–118 (2000).

Alster et al., "Treatment of Port–Wine Stains with the Flashlamp–pumped Pulsed Dye Laser: Extended Clinical Experience in Children and Adults", *Ann. Plast. Surg.,* 32(5):478–484 (1994).

Altshuler et al., "Extended Theory of Selective Photothermolysis", *Lasers Surg. Med.,* 29:416–432 (2001).

Ambrose et al., "Prospective randomized comparison of photocoagulation and rubber band ligation in treatment of haemorrhoids", *Br. Med. J.,* 286:1389–1391 (1983).

Anderson et al., "Mechanisms of Selective Vascular Changes Caused by Dye Lasers", *Lasers Surg. Med.,* 3:211–215 (1983).

Anderson et al., "Microvasculature Can be Sensitively Damaged Using Dye Lasers: A Basic Theory and Experimental Evidence in Human Skin", *Lasers Surg. Med.,* 1:263–276 (1981).

Anderson et al., "Selective Photothermolysis: Precise Microsurgery by Selective Absorption of Pulsed Radiation", *Science,* 220:524–527 (1983).

Anderson, T.F., "Light Sources in Photomedicine", in *Clinical Photomedicine,* Chapter 3, pp. 37–58, Marcel Dekker, Inc., New York (1993).

Angermeier, M.C., "Treatment of facial vascular lesions with intense pulsed light",*J. Cutan. Laser Ther.,* 1:95–100 (1999).

Anvari et al., "Selective cooling of biological tissues: application for thermally mediated therapeutic procedures", *Phys. Med. Biol.,* 40:241–252 (1995).

Apfelberg et al., "Comparison of Argon and Carbon Dioxide Laser for Treatment of Decorative Tattoos Clinical and Pathological Observations", *Lasers Surg. Med.,* 3:183 (Abstract No. 294) (1983).

Apfelberg et al., Dot or Pointillistic Method for Improvement in Results of Hypertrophic Scarring in the Argon Laser Treatment of Portwine Hemangiomas, *Lasers Surg. Med.,* 6:552–558 (1987).

Apfelberg et al., "Investigation of YAG Laser Uses in Plastic Surgery", *Lasers Surg.,* 6:246 (Abstract No. 77) (1986).

Apfelberg et al., "Preliminary Investigation of KTP/532 Laser Light in the Treatment of Hemangiomas and Tattoos", *Lasers Surg. Med.,* 6:38–42 (1986).

Apfelberg et al., "Progress Report on Extended Clinical Use of the Argon Laser for Cutaneous Lesions", *Lasers Surg. Med.*, 1:71–83 (1980).

Apfelberg et al., "Progress Report on Multicenter Study of Laser–Assisted Liposuction", *Aesth. Plast. Surg.*, 18:259–264 (1994).

Apfelberg et al., "Results of Argon and CO2 Laser Exposure of Telangiectasia of the Lower Extremity: A Preliminary Report", *Lasers Surg. Med.*, 3:149 (Abstract No. 165) (1983).

Apfelberg et al., "Study of Three Systems for Treatment of Superficial Varicosities of the Lower Extremity", *Lasers Surg. Med.*, 7:219–223 (1987).

Apfelberg et al., "Superpulse $CO_2$ Laser Treatment of Facial Syringomata", *Lasers Surg. Med.*, 7:533–537 (1987).

Apfelberg et al., "Update on Laser Usage in Treatment of Decorative Tattoos", *Lasers Surg. Med.*, 2:169–177 (1982).

Apfelberg, D.B., "Intralesional Laser Photocoagulation—Steroids as an Adjunct to Surgery for Massive Hemangiomas and Vascular Malformations", *Ann. Plast. Surg.*, 35:144–148 (1995).

Ara et al., "Irradiation of Pigmented Melanoma Cells with High Intensity Pulsed Radiation Generates Acoustic Waves and Kills Cells", *Lasers Surg. Med.*, 10:52–59 (1990).

Ashinoff et al., "Cappillary Hemangiomas and Treatment with the Flash Lamp–Pumped Pulsed Dye Laser", *Arch. Dermatol.*, 127:202–205 (1991).

Ashinoff et al., "Flashlamp–pumped pulsed dye laser for port–wine stains in infancy: Earlier versus later treatment", *J. Am. Acad. Dermatol.*, 24:467–472 (1991).

Bell et al., "100 µsec pulsed $CO_2$ laser resurfacing of lower eyelids: Erythema and rhytides reduction", SPIE, 2970:360–366 (1997).

Broska et al., "Comparison of the Argon Tunable Dye Laser with the Flashlamp Pulsed Dye Laser in Treatment of Facial Telangiectasia", *J. Dermatol. Surg. Oncol.*, 20:749–753 (1994).

Brugmans et al., "Temperature Response of Biological Materials to Pulsed Non–Ablative $CO_2$ Laser Irradiation", *Lasers Surg. Med.*, 11:587–594 (1991).

Burson et al., "Gel de Transmission de Ultrasonidos: Estudio Comparitivo de Distintas Formulaciones", *Farm Hosp.*, pp. 394–399 (1991) (in Spanish, with English Abstract Only).

Cates, M.C., "A long pulse (5 µs) e–beam pumped XeF laser", *SPIE*, 1225:34–43 (1990).

Cates, M.C., "Excimer laser produced plasma studies", *SPIE*, 1279:102–111 (1990).

Chess et al., "Cool Laser Optics Treatment of Large Telangiectasia of the Lower Extremities", *J. Dermatol. Surg. Oncol.*, 19:74–80 (1993).

Chissler et al., "Tanning Beds Are Not Without Drawbacks", *FDA Consumer*, pp. 21–22 (1984).

Cliff et al., "Treatment of mature port wine stains with the PhotoDerm VL",*J. Cutan. Laser Ther.*, 1:101–104 (1999).

Cole–Beuglet et al., "Ultrasound mammography for the Augmented Breast", *Radiology*, 146:737–742 (1983).

Colver et al., "Port Wine Stains", *J. Roy. Soc. Med.*, 80:603 (1987).

Colver et al., "Precise dermal damage with an infrared coagulator", *Br. J. Dermatol.*, 114:603–608 (1986).

Colver et al., "Tattoo removal using infra–red coagulation", *Br. J. Dermatol*, 112:481–485 (1985).

Colver G.B., "The Infrared Coagulator in Dermatology", *Dermatologic Clinics*, 7(1):155–167 (1989).

Daniell et al., "A History of Photodynamic Therapy", *Aust. N. Z. J. Surg.*, 61:340–348 (1991).

Denham et al., "Light Distribution in Laser Irradiated Tissue", *Lasers Surg. Med.*, 5:141 (Abstract No. 21) (1985).

Dzubow et al., "Leg Veins and Stretch Marks", *Am. Soc. Dermatol. Surg.*, 22:321 (1996).

Efthymiopoulos et al., "High–energy Short–pulse Flashlamps: Operating Characteristics", *Applied Optics*, 16:70–75 (1977).

Ell et al., "Laser Lithotripsy of Gallstone by Means of a Pulsed Neodymium YAG Laser—In Vitro and Animal Experiments", *Endoscopy*, 18:92–94 (1986).

Englehardt et al., "Spectroscopy During Laser Induced Shock Wave Lithotripsy",*SPIE*, 906:200–204 (1988).

Fitzpatrick et al., "Flashlamp–pumped Pulsed Dye Laser Treatment of Port–Wine Stains", *J. Dermatol. Surg. Oncol.*, 20:743–748 (1994).

Fitzpatrick et al., "Treatment of Leg Veins: A Comparison of Laser Therapy with a Noncoherent, Multiwave Light Source", *Proc. Ann. Meeting IEEE Lasers &Electro–Optics Soc*, pp. 238–239 (1993).

Flock et al., "Er:YAG Laser–Induced Changes in Skin In Vivo And Transdermal Drug Delivery", *SPIE*, 2970:374–379 (1997).

Flock et al., "Thermal Damage of Blood Vessels in Rat Skin–flap Window Chamber Using Indocyanine Green and a Pulsed Alexandrite Laser: A Feasibility Study", *Lasers Med. Sci.*, 8:185–196 (1993).

Foster et al., "The Successful Use of the PhotoDerm VL in the Treatment of a Cavernous Hemangioma in a Dark–Skinned Infant", *Minimally Invasive Surgical Nursing*, 10:102–104 (1996).

Garden et al., "Effect of Dye Laser Pulse Duration on Selective Cutaneous Vascular Injury", *J. Invest. Dermatol.*, 87(5):653–657 (1986).

Garden et al., "The Treatment of Port–wine Stains by the Pulsed Dye Laser: Analysis of Pulse Duration and Long–term Therapy", *Arch. Dermatol.*, 124:889–896 (1988).

Geronemus et al., "The Medical Necessity of Evaluation and Treatment of Port–Wine Stains", *J. Dermatol. Surg. Oncol.*, 17:76–79 (1991).

Gijsbers et al., "CW Laser Ablation Velocities as a Function of Absorption in an Experimental One–Dimensional Tissue Model", *Lasers Surg. Med.*, 11:287–296 (1991).

Gijsbers et al., "Effect of Force on Ablation Depth for a XeCl Excimer Laser Beam Delivered by an Optical Fiber in Contact with Arterial Tissue Under Saline", *Lasers Surg. Med.*, 12:576–584 (1992).

Gilbert, D.J., "Incorporating Photodynamic Therapy Into a Medical and Cosmetic Dermatology Practice", *Dermatol. Clin.*, 25:111–118 (2007).

Gold et al., "5–Aminolevulinic Acid Photodynamic Therapy: Where We Have Been and Where We Are Going", *Dermatol. Surg.*, 30:1077–1084 (2004).

Gold et al., "One–Year Follow–Up Using an Intense Pulsed Light Source for Long–Term Hair Removal", *J. Cutan. Laser Ther.*, 1:167–171 (1999).

Gold et al., "Treatment of Wrinkles and Skin Tightening Using Aluma™ Skin Renewal System with FACES™ (Functional Aspiration Controlled Electrothermal Stimulation) Technology",*Aesthetic Buyers Guide*, pp. 1–6 (2005).

Gold, M.H., "Aminolevulinic Acid Photodynamic Therapy: Medical Evidence for Its Expanded Use", *Expert Rev. Med. Devices*, 3:357–371 (2006).

Gold, M.H., "Introduction to Photodynamic Therapy: Early Experience",*Dermatol. Clin.*, 25:1–4 (2007).

Goldberg et al., "Nonablative Treatment of Rhytids With Intense Pulsed Light", *Lasers Surg. Med.*, 26:196–200 (2000).

Goldberg et al., "Q–switched Nd:YAG Laser: Rhytid Improvement by Non–Ablative Dermal Remodeling", *J. Cutan. Laser Ther.*, 2:157–160 (2000).

Goldberg, D.J., "Effect of Temperature–Controlled Cooling on Light–Based Skin Treatments", *J. Cos. Laser Ther.*, 8:155–156 (2006).

Goldberg, D.J., "Erbium: YAG Laser Resurfacing: What Is Its Role?",*Aesth. Surg. J.*, 18(4):255–260 (1998).

Goldberg, D.J., "New Collagen Formation After Dermal Remodeling with an Intense Pulsed Light Source", *J. Cutan. Laser Ther.*, 2:59–61 (2000).

Goldman et al., "600 nm Flash Pumped Dye Laser for Fragile Telangiectasia of the Elderly",*Lasers Surg. Med.*, 13:227–233 (1993).

Goldman et al., "Photothermal Sclerosis of Leg Veins", *Dermatol. Surg.*, 22:323–330 (1996).

Goldman et al., "Pulsed dye laser treatment of telangiectases with and without subtherapeutic sclerotherapy", *J. Am. Acad. Dermatol.*, 23(1):23–30 (1990).

Goldman et al., "Treatment of Cutaneous Vascular Lesions", in *Cutaneous Laser Surgery*, Chapter 2, pp. 19–105 (1994).

Goldman et al., "Treatment of port–wine stains (capillary malformation) with the Flashlamp–pumped pulsed dye laser",*J. Pediatrics*, 122(1):71–77 (1993).

Goldman, M.P., "Laser and Noncoherent Pulsed Light Treatment of Leg Telangiectasia and Venules", *Cos. Dermatol.*, 8(10):43–44 (1995).

Goldman, M.P., "Sclerotherapy Treatment for Varicose and Telangiectatic Leg Veins", in *Vascular and Pigmented Abnormalities*, Chapter 17, pp. 256–271 (1997).

Gomer, H., "Military laser burns away skin flaws",*The London Sunday Times*, No. 8929 (Oct. 15, 1995).

Gonzalez et al., "Treatment of telangiectases and other benign vascular lesions with the 577 nm pulsed dye laser",*J. Am. Acad. Dermatol.*, 27(2):220–226 (1992).

Gregory et al., "Effect of Blood Upon the Selective Ablation of Atherosclerotic Plaque with a Pulsed Dye Laser", *Lasers Surg. Med.*, 10:533–543 (1990).

Grevelink et al., "Update on the Treatment of Benign Pigmented Lesions with the Q–Switched Ruby Laser", *Lasers Surg. Med.*, 4:73–74 (Abstract No. 326) (1992).

Groot et al., "Comparison of the infrared coagulator and the carbon dioxide laser in the removal of decorative tattoos", *J. Am. Acad. Dermatol.*, 15:518–522 (1986).

Gustafsson et al., "A Variable Pulsewidth Vascular System for Dermatology",*SPIE*, 2128:188–196 (1994).

Guttman, C., "Novel radiofrequency–based treatment achieves skin tightening with minimal discomfort", http://www.modernmedicine.com, pp. 1–3 (2005).

Harris et al., "Facial skin resurfacing with a very short pulsed $CO_2$ laser: Beam characterization and initial histological results", *SPIE*, 2671:211–218 (1996).

Henderson, B.W., "Photodynamic therapy—coming of age", *Photodermatology*, 6:200–211 (1989).

Henning et al., "Clinical and Histological Evaluation of Portwine Stain Treatment with a Microsecond pulsed Dye–laser at 577 NM", *Lasers Surg. Med.*, 4:375–380 (1984).

Henning et al., "Port Wine Stain Coagulation Experiments with a 540–nm Continuous Wave Dye–laser", *Lasers Surg. Med.*, 2:205–210 (1983).

Henning et al., "Rhinophyma Treated by Argon Laser",*Lasers Surg. Med.*, 2:211–215 (1983).

Henning et al., "Treatment of Keloids and Hypertrofic Scars with an Argon Laser",*Lasers Surg. Med.*, 6:72–75 (1986).

Hilsenrath, J.E., "Investing it; Unsightly Veins? Zap. Wall St. Woes? Zap.", *New York Times*, http://www.nytimes.com, pp. 1–3 (Jun. 23, 1996).

Hruza et al., "Laser Skin Resurfacing", *Arch. Dermatol.*, 132:451–455 (1996).

Hughes, P.S.H., "Multiple Miliary Osteomas of the Face Ablated With the Erbium: YAG Laser",*Arch. Dermatol.*, 135:378–380 (1999).

"Infrared–Coagulator", Lumatec product leaflet, pp. 1–4.

Ishimaru, A., "Diffusion of light in turbid material",*Applied Optics*, 28(12):2210–2215 (1989).

Jacques, S.L., "The Role of Skin Optics in Diagnostic and Therapeutic Uses of Lasers", *Lasers Dermatol.*, pp. 1–21 (1992).

Jaitly et al., "1 MV Long Pulse Generator with Low Ripple and Low Droop", $8^{th}$ *IEEE Int'l Pulsed Power Conf.*, pp. 161–165 (1991).

Jaitly et al., "Design and Testing of Multi–output 300kV Prototype Induction Cell Pulsed Power Supply for Darht", $10^{th}$ *IEEE Int'l Pulsed Power Conf.*, pp. 1412–1421 (1995).

Jay, H.H., "Victory Over Veins", http://www.nytimes.com, pp. 1–2 (Jul. 21, 1996).

Johannigmann et al., "Ein Neues Ultraschall–Kontaktgel", *Gerburtsh. U. Frauenheilk*, p. 34 (1974) (in German, with English Abstract Only).

Kalka et al., "Photodynamic Therapy in Dermatology",*J. Am. Acad. Dermatol.*, 42:389–413 (2000).

Kaminester, L.H., "Suntanning Centers", *JAMA*, 244(11):1258–1259 (1980).

Kaufmann et al., "Pulsed 2·94–μm erbium–YAG laser skin ablation–experimental results and first clinical application", *Clin. Exp. Dermatol.*, 15:389–393 (1990).

Keijzer et al., "Laser Beam Diameter for Port Wine Stain Treatment", *Lasers Surg. Med.*, 11:601–605 (1991).

Kennedy et al., "Photodynamic Therapy with Endogenous Protoporphyrin, IX: Basic Principles and Present Clinical Experience", *J. of Photochem. Photobio.*, 6:143–148 (1990).

Kilmer et al., "Pulse Dye Laser Treatment of Rhytids", *Lasers Surg. Med.*, p. 44 (Abstract No. 194) (1997).

Koechner, W., in *Solid State Laser Engineering*, Springer Series in Optical Sciences—Vol. 1, Chapters 1–2, pp. 1–620, Springer–Verlag, New York (1976).

Lakmaker et al., "Modeling the Color Perception of Port Wine Stains and Its Relation to the Depth of Laser Coagulated Blood vessels", *Lasers Surg. Med.*, 13:219–226 (1993).

Lash et al., "How We Got Here", *Lasers Surg. Med.*, 3:113 (Abstract No. 29) (1983).

Lask et al., "Laser Skin Resurfacing with the SikTouch Flashscanner for Facial Rhytides", *Dermatol. Surg.*, 21:1021–1024 (1995).

Lask et al., "Nonablative laser treatment of facial rhytides", *SPIE*, 2970:338–349 (1997).

Levins et al., "Q–Switched Ruby Laser Treatment of Tattoos",*Lasers Surg Med.*, Suppl. 3:63–64 (Abstract No. 255) (1991).

Lowe et al., "Skin Resurfacing with the Ultrapulse Carbon Dioxide Laser",*Dermatol. Surg.*, 21:1025–1029 (1995).

Magee et al., "Vein Marking Through Ultrasound Coupling Gel",*Eur. J. Vasc. Surg.*, 4:491–492 (1990).

Majaron et al., "Deep Coagulation of Dermal Collagen with Repetitive Er: YAG Laser Irradiation", *Lasers Surg. Med.*, 26:215–222 (2000).

Majaron et al., "Er:YAG Laser Skin Resurfacing Using Repetitive Long–Pulse Exposure and Cryogen Spray Cooling: I. Histological Study", *Lasers Surg. Med.*, 28:121–130 (2001).

Majaron et al., "Er:YAG Laser Skin Resurfacing Using Repitative Long–Pulse Exposure and Cryogen Spray Cooling: II. Theoretical Analysis", *Lasers Surg. Med.*, 28:131–137 (2001).

Margolis et al., "Visible Action Spectrum for Melanin–Specific Selective Photothermolysis", *Lasers Surg. Med.*, 9:389–397 (1989).

Marhic et al., "White–Light Flashlamp–pumped dye laser for photography through endoscopes",*Optics Communications*, 45(1):21–25 (1983).

McCaughan et al., "Photodynamic Therapy for Cutaneous and Subcutaneous Malignant Neoplasms", *Arch. Surg.*, 124:211–216 (1989).

McCaughan et al., "Photodynamic Therapy: An Eight–Year Experience", in *Photodynamic Therapy: Basic Principles and Clinical Applications*, pp. 323–331 (1992).

Meijering et al., "Limits of Radial Time Constants to Approximate Thermal Response of Tissue", *Lasers Surg. Med.*, 13:685–687 (1993).

Miller et al., "Optical Modelling of Light Distributions in Skin Tissue Following Laser Irradiation", *Lasers Surg. Med.*, 13:565–571 (1993).

Milner et al., "Analysis of nonablative skin resurfacing", *SPIE*, 2970:367–373 (1997).

Mordon et al., "Rationale for Automatic Scanners in Laser Treatment of Port wine Stains", *Lasers Surg. Med.*, 13:113–123 (1993).

Morelli et al., "Tunable Dye Laser (577 nm) Treatment of Port Wine Stains", *Lasers Surg. Med.*, 6:94–99 (1986).

Motamedi et al., "Thermal Response of Tissue During Laser Angioplasty", *Lasers Surg. Med.*, 5:172 (Abstract No. 114) (1985).

Mutzhas et al., "A New Apparatus with High Radiation Energy Between 320–460 nm: Physical Description and Dermatological Applications", *J. Invest. Dermatol.*, 76:42–47 (1981).

Nakagawa et al., "Ultrastructural Changes in Human Skin After Exposure to a Pulsed Laser", *J. Invest. Dermatol.*, 84(5):396–400 (1985).

Nestor et al., "New Perspectives on Photorejuvenation", *Skin & Aging*, 11:68–74 (2003).

Newman et al., "Variable Pulse Erbium: YAG Laser Skin Resurfacing of Perioral Rhytides and Side–by–side Comparison with Carbon Dioxide Laser", *Lasers Surg. Med.*, 26:208–214 (2000).

Parrish et al., "Exploring Mechanisms of Specificity in Laser–Tissue Interactions", *Lasers Surg. Med.*, 3:175 (Abstract No. 260) (1983).

Parrish et al., "Spatial Confinement of Thermal Effects of Pulsed Laser Irradiation of Tissue", *Lasers Surg. Med.*, 3:157 (Abstract No. 195) (1973).

Paul et al., "The Effect of Temperature and Other Factors on Selective Microvascular Damage Caused by Pulsed Dye Laser",*J. Invest. Dermatol.*, 81(4):333–336 (1983).

Pfefer et al., "Mechanisms of Laser–Induced Thermal Coagulation of Whole Blood in vitro", *SPIE*, 3590:20–31 (1999).

Philipp et al., "Treatment of Congenital Vascular Disorders: Classification, Step Programme and Therapeutical Procedures", *SPIE*, 2086:228–238 (1993).

Pickering et al., "585 nm for the Laser Treatment of Port Wine Stains: A Possible Mechanism", *Lasers Surg., Med.*, 11:616–618 (1991).

Plewig et al., "A new apparatus for the delivery of high intensity UVA and UVA+ UVB irradiation, and some dermatological applications", *Br. J. Dermatol.*, 98:15–24 (1978).

Polla et al., "Tunable Pulsed Dye Laser for the Treatment of Benign Cutaneous Vascular Ectasia", *Dermatologica*, 174:11–17 (1987).

Pottier et al., "Assessment of Non–Coherent Light Sources for Photodynamic Therapy", *SPIE*, 2371:364–368 (1995).

Pratesi, R., "Potential Use of Incoherent and Coherent Light–Emitting–Diodes (LEDs) in Photomedicine", in *Photomedicine, Laser Photobiol. Photomed.*, 22:293–308 (1983).

Ramrus et al., "A Compact One–Half MV Rep–Rate Pulser", $20^{th}$ *IEEE Power Modulator Symposium*, pp. 68–71 (1992).

Ramrus et al., "Design and Performance of a One–Half MV Rep–Rate Pulser", Proc. Of the $8^{th}$ IEEE International Pulsed Power Conference, pp. 982–985 (1991).

Ranganathan et al., "Promises for Ultrasonic Waves on Activity of Silica Gel and Some Supported Catalystes", *Ind. Eng. Chem. Prod. Res. Develop.*, 12:155–158 (1973).

Rassing et al., "Measurement of Ultrasonic Absorption in a Gel by Light Diffraction and Resonator Methods", *J. Mol. Liq.*, 26:97–108 (1983).

Rastegar et al., "Technique for Measurement of One–Dimensional Instantaneous Ablation Velocity", *Lasers Surg. Med.*, 8:533–535 (1988).

Raulin et al., "Treatment of a Nonresponding Port–Wine Stain With a New Pulsed Light Source (PhotoDerm® VL)", *Lasers Surg. Med.*, 21:203–208 (1997).

Raulin et al., "Treatment of Adult Port–Wine Stains Using Intense Pulsed Light Therapy (PhotoDerm VL): Brief Initial Clinical Report", *Dermatol. Surg.*, 23:594–601 (1997).

Raulin et al., "Treatment of benign venous malformations with an intense pulsed light source (PhotoDerm VL)", *Eur. J. Dermatol.*, 7:279–282 (1997).

Raulin et al., "Treatment of Essential Telangiectasias with an Intense Pulsed Light Source (PhotoDerm VL)", *Dermatol. Surg.*, 23:941–946 (1997).

Raulin et al., "Treatment of Port–wine Stains With a Noncoherent Pulsed Light Source", *Arch. Dermatol.*, 135:679–683 (1999).

Reyes et al., "Treatment of port–wine stains during childhood with the flashlamp–pumped pulsed dye laser", *J. Am. Acad. Dermatol.*, 23:1142–1148 (1990).

Ross et al., "Effects of $CO_2$ Laser Pulse Duration in Ablation and Residual Thermal Damage: Implications for Skin Resurfacing", *Lasers Surg. Med.*, 19:123–129 (1996).

Rowe, P.M., "Photodynamic therapy begins to shine", *Lancet*, 351:1496 (1998).

Sadick et al., "Photorejuvenation with Intense Pulsed Light: Results of a Multi–Center Study", *J. Drugs Dermatol.*, 3(1):41–49 (2004).

Sadick, N.S., "A Structural Approach to Nonablative Rejuvenation", *Cosmetic Dermatol.*, 15(12):39–43 (2002).

Sadick, N.S., "Update on Non–Ablative Light Therapy for Rejuvenation: A Review", *Lasers Surg. Med.*, 32:120–128 (2003).

Schamiloglu et al., "Modern Pulsed Power: Charlie Martin and Beyond", *Proceedings of the IEEE*, 92(7): 1014–1020 (2004).

Schroeter et al., "An Intense Light Source: The Photoderm VL–Flashlamp as a New Treatment Possibility for Vascular Skin Lesions", *Dermatol. Surg.*, 24:743–748 (1998).

Schroeter et al., "Clinical significance of an intense, pulsed light source on leg telangiectasias of up to 1mm diameter", *Eur. J. Dermatol.*, 7:38–42 (1997).

Schroeter et al., "Photoderm VL treatment of leg teleangiectasia",*JEADV*, 5(Suppl. 1):S49 (Abstract No. W76) (1995).

Schwimer et al., "The Effect of Ultrasound Coupling Gels on Sperm Motility In Vitro",*Fertil. Steril.*, 42:946–947 (1984).

Sheean et al., "Arrest of Embryo Development by Ultrasound Coupling Gels", *Fertil. Steril.*, 45:568–571 (1986).

Smith et al., "532–Nanometer Green Laser Beam Treatment of Superficial Varicosities of the Lower Extremities", *Lasers Surg. Med.*, 8:130–134 (1988).

Steiger et al., "Comparison of Different Pulsed and Q–switched Solid–state Laser Systems for Endoscopic Laser Induced Shock Wave Lithotripsy: Performance and Laser/Stone Interactions", *SPIE*, 2300:94–101 (1990).

Strickland et al., "A 5kV, 250 kA Rep–Rated Pulser Using Parallel Ignitrons", *7th IEEE Int'l Pulsed Conf.*, pp. 729–731 (1989).

Sunde et al., "Traumatic Tattoo Removal: Comparison of Four Treatment Methods in an Animal Model with Correlation to Clinical Experience", *Lasers Surg. Med.*, 10:158–164 (1990).

Svaasand et al., "Light and Drug Distribution with Topically Administered Photosensitizers", *Lasers Surg., Med.* 11:261–265 (1996).

Szeimies et al., "A Possible New Incoherent Lamp for Photodynamic Treatment of Superficial Skin Lesions", *Acta Derm. Venereol (Stockh).*, 74:117–119 (1994).

Tan et al., "Action Spectrum of Vascular Specific Injury Using Pulsed Irradiation", *J. Invest. Dermatol.*, 92(6):868–871 (1989).

Tan et al., "EMLA for Laser Treatment of Portwine Stains in Children", *Lasers Surg. Med.*, 12:543–548 (1992).

Tan et al., "Histologic Responses of Port–wine Stains Treated by Argon, Carbon Dioxide, and Tunable Dye Lasers", *Arch. Dermatol.*, 122:1016–1022 (1986).

Tan et al., "Pulsed Dye Laser Treatment of Recalcitrant Verrucae: A Preliminary Report", *Lasers Surg. Med.*, 13:127–137 (1993).

Tan et al., "Treatment of Children with Port–Wine Stains Using the Flashlamp–Pulsed Tunable Dye Laser", *N. Engl. J. Med.*, 320(7):416–421 (1989).

Taub, A.F., "Photodynamic Therapy: Other Uses", *Dermtol. Clin.*, 25:101–109 (2007).

Taylor et al., "Q–Switched Ruby Laser (QSRL) Irradiation of Benign Pigmented Lesions: Dermal vs. Epidermal", *Lasers Surg. Med.*, 3:65 (Abstract No. 262) (1991).

Templeton et al., "Comparison of infrared coagulation and rubber band ligation for first and second degree haemorrhoids: a randomized prospective clinical trial", *Br. Med. J.*, 286:1387–1389 (1983).

Troccoli et al., "Multiple–Pulse Photocoagulation of Blood Vessels With A 585 Nm Tunable Laser", *Lasers Surg. Med.*, 4:3 (Abstract No. 2) (1992).

van Gemert et al., "Can Physical Modeling Lead to an Optimal Laser Treatment Strategy for Port–Wine Stains", in *Laser Applications in Medicine and Biology*, Chapter 5, pp. 199–247, Plenum Press, New York (1991).

van Germert et al., "Instantaneous Ablation Behavior of In–Vitro Rods During Laser Irradiation", *Lasers Surg. Med.*, 5:136 (Abstract No. 4) (1985).

van Germert et al., "Is There an Optimal Laser Treatment for Port Wine Stains?", *Lasers Surg. Med.*, 6:76–83 (1986).

van Germert et al., "Wavelengths for Laser Treatment of Port Wine Stains and Telangiectasia", *Lasers Surg. Med.*, 16:147–155 (1995).

"Varicose Vein Device Producer comes to U.S. Market", *Clinica*, 687:9 (Jan. 8, 1996).

Venning et al., "Tattoo removal using infra–red coagulation: a dose comparison", *Br. J. Dermatol.*, 117:99–105 (1987).

Wagner et al., "Percutalgine–Gel et Ultrasonotherapie en Pathologie du Sport", *La Revue de Medecine*, 32:1681–1683 (1992) (in French, with English Abstract Only).

Waldorf et al., "Skin Resurfacing of Fine to Deep Rhytides Using a Char–free Carbon Dioxide Laser in 47 Patients", *Dermatol. Surg.*, 21:940–946 (1995).

Walsh et al., "Er:YAG Laser Ablation of Tissue: Measurement of Ablation Rates", *Lasers Surg. Med.*, 9:327–337 (1989).

Walsh et al., "Pulsed $CO_2$ Laser Tissue Ablation: Effect of Tissue Type and Pulse Duration On Thermal Damage", *Lasers Surg. Med.*, 8:108–118 (1988).

Walsh, J.T., "Er:YAG Laser Ablation of Tissue: Effect of Pulse Duration and Tissue Type on Thermal Damage", *Lasers Surg. Med.*, 9:314–326 (1989).

Walsh, J.T., "Pulsed Laser Ablation of Tissue: Analysis of the Removal Process and Tissue Healing", *Unpublished Ph.D. dissertation Massachusetts Institute of Technology, on file with Institute Archives and Hayden Library, Massachusetts Institute of Technology*, pp. 1–312 (1988).

Weiss et al., "Rejuvenation of Photoaged Skin: 5 Years Results with Intense Pulsed Light of the Face, Neck, and Chest", *Dermatol. Surg.*, 28:1115–1119 (2002).

Welch et al., "Practical Models for Light Distribution in Laser–Irradiated Tissue", *Lasers Surg. Med.*, 6:488–493 (1987).

Werner et al., "Die Hamangiombehandlung mit dem Neodym: Yttrium–Aluminium–Granat Laser (Nd:YAG–Laser)", *Laryngo–Rhino–Otol.*, 71:388–395 (1992), (in German, with English Abstract Only).

West, T., "How Laser Surgery Can Help Your Rosacea Patients", *Skin & Aging*, pp. 43–46 (1998).

Wilder, D., "Pulsed 1064–nm Nd:YAG Laser Therapy for Noninvasive Treatment of a Massive Hemangioma: Case Report", *J. Clin. Laser Med. Surg.*, 17(6):245–247 (1999).

Wilson et al., "The physics of photodynamic therapy", *Phys. Med. Biol.*, 31(4):327–360 (1986).

EX PARTE
REEXAMINATION CERTIFICATE
ISSUED UNDER 35 U.S.C. 307

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is cancelled.

New claims 3–84 are added and determined to be patentable.

Claim 2 was not reexamined.

3. *A method for applying electromagnetic radiation to the skin using a flashlamp disposed in a hand-held unit, the method comprising:*
   *controlling the flashlamp using a microprocessor and a power source located in a control box;*
   *providing power to the flashlamp using the power source and a flexible cable that is configured to transfer electrical pulses from the power source to the flashlamp;*
   *generating, using the flashlamp, pulses of electromagnetic radiation having a pulse width of about 5 to about 50 milliseconds, each of the pulses of electromagnetic radiation comprising a plurality of wavelengths ranging over the visible section of the electromagnetic spectrum and over at least parts of the ultra-violet and infra-red sections of the electromagnetic spectrum;*
   *filtering a substantial part of the plurality of wavelengths in the ultra-violet section of the electromagnetic spectrum, thereby producing filtered electromagnetic radiation ranging over a substantial part of the visible and at least part of the infra-red sections of the generated electromagnetic radiation, wherein the filtered electromagnetic radiation includes wavelengths of about 520 nm to about 1000 nm;*
   *applying the filtered electromagnetic radiation generated by the flashlamp to at least 4 square centimeters of the skin using a rectangular light guide disposed proximate to the skin.*

4. *The method of claim 3 wherein generating pulses of electromagnetic radiation includes generating pulses as a function of a level of pigmentation of the skin.*

5. *The method of claim 3 wherein filtering includes filtering the electromagnetic radiation as a function of a level of pigmentation of the skin.*

6. *The method of claim 3 further comprising collimating the electromagnetic radiation.*

7. *The method of claim 3 wherein providing power to the flashlamp includes providing power using at least one pulse forming network.*

8. *The method of claim 3 wherein providing power to the flashlamp includes providing power using a driver circuit.*

9. *The method of claim 8 wherein providing power to the flashlamp includes providing power using a voltage source, a capacitor bank, an inductor, a diode, and a switch.*

10. *The method of claim 3 further comprising concentrating the electromagnetic radiation using a reflector.*

11. *The method of claim 3 further comprising controlling a spectrum of electromagnetic radiation generated by the flashlamp by varying at least one of a voltage and a current provided to the flashlamp.*

12. *The method of claim 3 further comprising pre-discharging the flashlamp.*

13. *The method of claim 3 further comprising removing hair growing on the skin using the filtered electromagnetic radiation.*

14. *The method of claim 3 wherein:*
    *controlling the flashlamp includes controlling a plurality of flashlamps;*
    *providing power to the flashlamp includes providing power to a plurality of flashlamps; and*
    *generating pulses of electromagnetic radiation includes generating radiation using a plurality of flashlamps.*

15. *The method of claim 3 wherein filtering a substantial part of the plurality of wavelengths is performed using a removable filter.*

16. *The method of claim 3 further comprising providing a simmer current to the flashlamp.*

17. *The method of claim 3 wherein applying the filtered electromagnetic radiation includes applying electromagnetic radiation having a wavelength of about 550 to about 1000 nm.*

18. *The method of claim 3 wherein applying the filtered electromagnetic radiation includes applying electromagnetic radiation having a wavelength of about 520 to about 650 nm.*

19. *The method of claim 3 wherein applying the filtered electromagnetic radiation includes applying electromagnetic radiation having a wavelength of about 520 to about 700 nm.*

20. *The method of claim 3 wherein applying the filtered electromagnetic radiation includes applying electromagnetic radiation having a wavelength of about 600 to about 1000 nm.*

21. *The method of claim 3 wherein applying the filtered electromagnetic radiation includes applying electromagnetic radiation having a wavelength of about 650 to about 950 nm.*

22. *The method of claim 3 wherein applying the filtered electromagnetic radiation includes applying a train of pulses, wherein a delay between each of the pulses is at least 5 milliseconds.*

23. *The method of claim 3 wherein:*
    *applying the filtered electromagnetic radiation includes applying electromagnetic radiation having only a substantially near-infrared wavelength;*
    *generating pulses of electromagnetic radiation includes generating pulses having a pulse width selected from the group consisting of 30, 40, and 50 milliseconds; and*
    *applying the filtered electromagnetic radiation includes applying electromagnetic radiation to an area of skin of about 40 by 16 millimeters.*

24. *The method of claim 3 wherein:*
    *applying the filtered electromagnetic radiation includes applying electromagnetic radiation having a wavelength of about 650 to about 950 nm;*
    *generating pulses of electromagnetic radiation includes generating pulses having a pulse width selected from the group consisting of 30, 40, and 50 milliseconds; and*
    *applying the filtered electromagnetic radiation includes applying electromagnetic radiation to an area of skin of about 40 by 16 millimeters.*

25. The method of any one of claims 3–24 wherein applying the filtered electromagnetic radiation includes applying electromagnetic radiation to the skin having an energy density of about 6 to about 20 Joules per square centimeter.

26. A method for applying electromagnetic radiation to skin, the method comprising:
generating power pulses using a power supply circuit that includes a pulse forming network, a relay, and a high voltage power supply configured to provide at least one voltage between 500 and 5000 volts, the power supply being disposed in a control unit;
controlling the generation of the power pulses using a microprocessor;
providing the power pulses to a flashlamp disposed in a hand-held unit via a flexible cable;
generating pulses of electromagnetic radiation having a plurality of wavelengths over the visible section of the electromagnetic spectrum and at least part of each of the ultra-violet and infra-red sections of the electromagnetic spectrum using a flashlamp, wherein each of the pulses of electromagnetic radiation is between about 5 to about 50 milliseconds in duration;
filtering, using a filter disposed between the flashlamp and a light guide, a substantial part of the ultra-violet radiation to produce filtered electromagnetic radiation ranging over at least a substantial part of the visible and at least part of the infra-red sections of the generated electromagnetic radiation, wherein the filtered electromagnetic radiation includes wavelengths of about 520 nm to about 1000 nm; and
applying the filtered electromagnetic radiation generated by the flashlamp to at least 4 square centimeters of the skin via the light guide when placed in proximity to the skin.

27. The method of claim 26 wherein generating the power pulses includes generating power pulses as a function of a level of pigmentation of the skin.

28. The method of claim 26 wherein filtering includes filtering the electromagnetic radiation as a function of a level of pigmentation of the skin.

29. The method of claim 26 further comprising collimating the electromagnetic radiation.

30. The method of claim 26 wherein generating the power pulses includes generating power pulses using a plurality of pulse forming networks.

31. The method of claim 26 further comprising providing a simmer current to the flashlamp.

32. The method of claim 26 further comprising concentrating the electromagnetic radiation using a reflector.

33. The method of claim 26 further comprising controlling the spectrum of electromagnetic radiation generated by the flashlamp by varying at least one of a voltage and a current provided to the flashlamp.

34. The method of claim 26 further comprising pre-discharging the flashlamp.

35. The method of claim 26 further comprising removing hair growing on the skin using the filtered electromagnetic radiation.

36. The method of claim 26 wherein the filtered electromagnetic radiation has a wavelength of about 550 to about 1000 nm.

37. The method of claim 26 wherein the filtered electromagnetic radiation has a wavelength of about 520 to about 650 nm.

38. The method of claim 26 wherein the filtered electromagnetic radiation has a wavelength of about 520 to about 700 nm.

39. The method of claim 26 wherein the filtered electromagnetic radiation has a wavelength of about 600 to about 1000 nm.

40. The method of claim 26 wherein generating power pulses includes generating a train of power pulses, wherein the delay between the power pulses is at least about 5 milliseconds.

41. The method of any one of claims 26–40 wherein applying the filtered electromagnetic radiation to the skin includes applying electromagnetic radiation to the skin having an energy density of about 6 to about 20 Joules per square centimeter.

42. A medical treatment system for applying electromagnetic radiation to the skin, the system comprising:
a control unit comprising:
a power supply configured to generate power pulses and including at least one pulse forming network, a relay, and a high voltage power supply configured to provide at least one voltage between 500 and 5000 volts;
a microprocessor configured to control the power supply;
a user interface coupled to the microprocessor;
a hand-held unit comprising:
a flashlamp for generating electromagnetic radiation having a plurality of wavelengths ranging over the visible section of the electromagnetic spectrum and over at least parts of the ultra-violet and infra-red sections of the electromagnetic spectrum;
a filter for filtering a substantial part of the plurality of wavelengths in the ultra-violet section of the electromagnetic spectrum to produce filtered electromagnetic radiation ranging over a substantial part of the visible and at least part of the infra-red sections of the generated electromagnetic radiation such that the filtered electromagnetic radiation includes wavelengths of about 520 nm to about 1000 nm;
a rectangular light guide configured to be placed in proximity of the skin and being configured for applying the filtered electromagnetic radiation generated by the flashlamp to at least 4 square centimeters of the skin; and
a flexible cable for coupling the control unit and the hand-held unit such that the power pulses are provided from the power supply to the flashlamp;
wherein the power supply is configured such that each pulse of electromagnetic radiation generated by the flashlamp is between about 5 to about 50 milliseconds in duration.

43. The system of claim 42 wherein the electromagnetic radiation is generated as a function of a level of pigmentation of the skin.

44. The system of claim 42 wherein the filter is configured as a function of a level of pigmentation of the skin.

45. The system of claim 42 further comprising a collimator for collimating the filtered electromagnetic radiation.

46. The system of claim 42 wherein the power supply comprises a plurality of pulse forming networks.

47. The system of claim 42 further comprising a simmer power supply configured to provide a simmer current to the flashlamp.

48. The system of claim 42 further comprising a reflector configured to concentrate the electromagnetic radiation.

49. The system of claim 42 wherein the microprocessor is configured to control the operation of the flashlamp by varying at least one of a voltage and a current provided by the power supply.

50. The system of claim 42 wherein the microprocessor is configured to cause a pre-discharge of the flashlamp.

51. The system of claim 42 wherein the filter is configured such that the filtered electromagnetic radiation has a wavelength of about 550 to about 1000 nm.

52. The system of claim 42 wherein the filter is configured such that the filtered electromagnetic radiation has a wavelength of about 520 to about 650 nm.

53. The system of claim 42 wherein the filter is configured such that the filtered electromagnetic radiation has a wavelength of about 520 to about 700 nm.

54. The system of claim 42 wherein the filter is configured such that the filtered electromagnetic radiation has a wavelength of about 600 to about 1000 nm.

55. The system of claim 42 wherein the microprocessor is configured to cause the flashlamp to generate a train of pulses of the electromagnetic radiation, wherein the delay between each of the train of pulses is at least about 5 milliseconds.

56. The system of claim 42 wherein:
the filter is configured to pass only substantially near-infrared wavelengths;
the microprocessor is configured such that the duration of each pulse of electromagnetic radiation generated by the flashlamp is selected from the group consisting of 30, 40, and 50 milliseconds; and
the light guide is configured for apply electromagnetic radiation to an area of skin that is substantially 40 by 16 millimeters.

57. The system of claim 42 wherein:
the filter is configured to pass only wavelengths that are about 650 to about 950 nm;
the microprocessor is configured such that the duration of each pulse of electromagnetic radiation generated by the flashlamp is selected from the group consisting of 30, 40, and 50 milliseconds; and
the light guide is configured to apply electromagnetic radiation to an area of skin that is substantially 40 by 16 millimeters.

58. The system of any one of claims 42–57 wherein the power supply is configured such that the electromagnetic radiation applied to the skin has an energy density of about 6 to about 20 Joules per square centimeter.

59. A method for applying electromagnetic radiation to skin, the method comprising:
generating power pulses using a power supply circuit disposed in a control unit, wherein the power supply circuit includes a pulse forming network, a relay, and a high voltage power supply configured to provide at least one voltage between 500 and 5000 volts;
controlling the generation of the power pulses using a microprocessor;
providing the power pulses to a flashlamp disposed in a hand-held unit via a flexible cable;
generating pulses of electromagnetic radiation over the visible spectrum and at least part of each of the ultra-violet and infra-red sections of the electromagnetic spectrum using a flashlamp, wherein each of the pulses of electromagnetic radiation is between about 5–50 milliseconds in duration;
filtering, using a filter disposed between the flashlamp and a light guide, a substantial part of the ultra-violet radiation to produce filtered electromagnetic radiation ranging over at least a substantial part of the visible and at least part of the infra-red sections of the generated electromagnetic radiation, wherein the filtered electromagnetic radiation has a wavelength of about 520 nm to about 1000 nm; and
applying the filtered electromagnetic radiation generated by the flashlamp to at least 3 square centimeters of the skin via the light guide when placed in proximity to the skin.

60. A method for applying electromagnetic radiation to the skin using a flashlamp, the method comprising:
controlling the flashlamp using a microprocessor and a power source located in a control box;
providing high-voltage power to the flashlamp using the power source and a flexible cable that is configured to transfer electrical pulses from the power source to the flashlamp;
generating, using the flashlamp, pulses of electromagnetic radiation having a plurality of wavelengths ranging over the visible section of the electromagnetic spectrum and over at least parts of the ultra-violet and infra-red sections of the electromagnetic spectrum;
filtering a substantial part of the plurality of wavelengths in the ultra-violet section of the electromagnetic spectrum using a cutoff filter having a cutoff point of less than about 400 nm, thereby producing filtered electromagnetic radiation ranging over a substantial part of the visible and at least part of the infra-red sections of the generated electromagnetic radiation; and
applying the filtered electromagnetic radiation generated by the flashlamp to at least 4 square centimeters of the skin using a rectangular light guide disposed proximate to the skin, wherein the filtered electromagnetic radiation applied to the skin includes wavelengths in the range of about 520 nm to about 1000 nm.

61. The method of claim 60 wherein generating pulses of electromagnetic radiation includes generating pulses as a function of a level of pigmentation of the skin.

62. The method of claim 60 wherein filtering includes filtering the electromagnetic radiation as a function of a level of pigmentation of the skin.

63. The method of claim 60 further comprising collimating the electromagnetic radiation.

64. The method of claim 60 wherein providing power to the flashlamp includes providing power using at least one pulse forming network.

65. The method of claim 60 wherein providing power to the flashlamp includes providing power using a driver circuit.

66. The method of claim 65 wherein providing power to the flashlamp includes providing power using a voltage source, a capacitor bank, an inductor, a diode, and a switch.

67. The method of claim 60 further comprising concentrating the electromagnetic radiation using a reflector.

68. The method of claim 60 further comprising controlling a spectrum of electromagnetic radiation generated by the flashlamp by varying at least one of a voltage and a current provided to the flashlamp.

69. The method of claim 60 further comprising pre-discharging the flashlamp.

70. The method of claim 60 further comprising removing hair growing on the skin using the filtered electromagnetic radiation.

71. The method of claim 60 wherein:
controlling the flashlamp includes controlling a plurality of flashlamps;
providing power to the flashlamp includes providing power to a plurality of flashlamps; and generating pulses of electromagnetic radiation includes generating radiation using a plurality of flashlamps.

72. The method of claim 60 wherein filtering a substantial part of the plurality of wavelengths is performed using a removable filter.

73. The method of claim 60 further comprising providing a simmer current to the flashlamp.

74. The method of claim 60 wherein applying the filtered electromagnetic radiation includes applying electromagnetic radiation having a wavelength of about 550 to about 1000 nm.

75. The method of claim 60 wherein applying the filtered electromagnetic radiation includes applying electromagnetic radiation having a wavelength of about 520 to about 650 nm.

76. The method of claim 60 wherein applying the filtered electromagnetic radiation includes applying electromagnetic radiation having a wavelength of about 520 nm to about 700 nm.

77. The method of claim 60 wherein applying the filtered electromagnetic radiation includes applying electromagnetic radiation having a wavelength of about 600 to about 1000 nm.

78. The method of claim 60 wherein applying the filtered electromagnetic radiation includes applying electromagnetic radiation having a wavelength of about 650 to about 950 nm.

79. The method of claim 60 wherein applying the filtered electromagnetic radiation includes applying a train of pulses, wherein a delay between each of the pulses is at least 5 milliseconds.

80. The method of claim 60 wherein each of the generated pulses of electromagnetic radiation has a duration of about 5 milliseconds to about 200 milliseconds.

81. The method of claim 60 wherein each of the generated pulses of electromagnetic radiation has a duration of about 5 milliseconds to about 100 milliseconds.

82. The method of claim 60 wherein each of the generated pulses of electromagnetic radiation has a duration of about 5 milliseconds to about 50 milliseconds.

83. The method of any one of claims 60–82 wherein applying the filtered electromagnetic radiation includes applying electromagnetic radiation to the skin having an energy density of about 6 to about 20 Joules per square centimeter.

84. The method of claim 60 further comprising coagulating blood using the electromagnetic radiation applied to the skin.

\* \* \* \* \*